US008466129B2

(12) United States Patent
Zeng et al.

(10) Patent No.: US 8,466,129 B2
(45) Date of Patent: Jun. 18, 2013

(54) METHOD OF PREVENTING AND TREATING AIRWAY REMODELING AND PULMONARY INFLAMMATION USING $A_{2B}$ ADENOSINE RECEPTOR ANTAGONISTS

(75) Inventors: Dewan Zeng, Palo Alto, CA (US); Michael R. Blackburn, Pearland, TX (US); Luiz Belardinelli, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 237 days.

(21) Appl. No.: 12/605,783

(22) Filed: Oct. 26, 2009

(65) Prior Publication Data

US 2010/0105706 A1 Apr. 29, 2010

Related U.S. Application Data

(63) Continuation of application No. 11/251,450, filed on Oct. 14, 2005, now abandoned.

(60) Provisional application No. 60/619,439, filed on Oct. 15, 2004.

(51) Int. Cl.
*A61K 31/67* (2006.01)

(52) U.S. Cl.
USPC .......... 514/81; 514/263.2; 514/244; 514/270; 544/270

(58) Field of Classification Search
USPC .................. 514/81, 263.2, 244, 270; 544/270
See application file for complete search history.

(56) References Cited

U.S. PATENT DOCUMENTS

| | | | |
|---|---|---|---|
| 6,117,878 A * | 9/2000 | Linden ...................... | 514/263.34 |
| 6,387,913 B1 * | 5/2002 | Mustafa ........................ | 514/44 |
| 6,806,270 B2 | 10/2004 | Biaggioni et al. | |
| 6,815,446 B1 | 11/2004 | Biaggioni et al. | |
| 6,825,349 B2 | 11/2004 | Kalla et al. | |
| 6,894,021 B2 | 5/2005 | Belardinelli et al. | |
| 6,916,804 B2 * | 7/2005 | Castelhano et al. ...... | 514/217.06 |
| 6,977,300 B2 * | 12/2005 | Kalla et al. ..................... | 544/269 |
| 7,105,665 B2 | 9/2006 | Kalla et al. | |
| 7,125,993 B2 | 10/2006 | Elzein et al. | |
| 7,304,070 B2 | 12/2007 | Kalla et al. | |
| 7,317,017 B2 | 1/2008 | Kalla et al. | |
| 7,449,473 B2 | 11/2008 | Kalla et al. | |
| 7,521,554 B2 | 4/2009 | Elzein et al. | |
| 7,625,881 B2 | 12/2009 | Kalla et al. | |
| 7,741,331 B2 | 6/2010 | Kalla et al. | |
| 7,795,268 B2 | 9/2010 | Zeng et al. | |
| 7,795,269 B2 | 9/2010 | Kalla et al. | |
| 2003/0139428 A1 | 7/2003 | Kalla et al. | |
| 2003/0162764 A1 * | 8/2003 | Castelhano et al. ....... | 514/210.2 |
| 2003/0229106 A1 * | 12/2003 | Kalla et al. ................. | 514/263.2 |
| 2003/0235555 A1 * | 12/2003 | Shealey et al. ............... | 424/85.1 |
| 2004/0176399 A1 | 9/2004 | Elzein et al. | |
| 2006/0058322 A1 | 3/2006 | Zeng et al. | |
| 2008/0318983 A1 | 12/2008 | Kalla et al. | |
| 2010/0056538 A1 | 3/2010 | Kalla et al. | |
| 2010/0222300 A1 | 9/2010 | Kalla et al. | |

FOREIGN PATENT DOCUMENTS

NZ 546266 A 10/2008

OTHER PUBLICATIONS

Pfizer, "Health info", 2003, http://www.pfizer.be/English/What_we_do/Health_info/COPD.htm.*
Office Action for NZ589656 mailed Dec. 7, 2010.
Office Action for NZ589657 mailed Dec. 7, 2010.
Office Action for EP 05808733.9, mailed Feb. 22, 2011.
Blackburn et al., "Adenosine Mediates IL-13-Induced Inflammation and Remodeling in the Lung and Interacts in an IL-13-Adenosine Amplification Pathway". J. Clin. Invest. 112:332-344 (2003), doi: 10.1172/JCI200316815.
Crimi et al., "Purine Derivatives in the Study of Allergic Inflammation in Respiratory Diseases". Allergy 1997; 52:48-54.
Cushley et al., "Inhaled Adenosine and Guanosine on Airway Resistance in Normal and Asthmatic Subjects", (1983) Br J Clin Pharmacol 15;161-165.
Driver et al., "Adenosine in Bronchoalveolar Lavage Fluid in Asthma". Am Rev Respir Dis, vol. 148, pp. 91-97, (1993).
Elias et al., "Airway Remodeling in Asthma". The Journal of Clinical Investigation, Oct. 1999, vol. 104, No. 8, pp. 1001-1006.
Feoktistov et al., "Adenosine A2B Receptors As Therapeutic Targets". Drug Development Research 45:198-206 (1998).
Feoktistov et al., "Adenosine A2B Receptors: A Novel Therapeutic Target in Asthma"? (1998) Trends Pharmacol Sci 19:148-153.
Feoktistov et al., "Hypoxia Modulates Adenosine Receptors in Human Endothelial and Smooth Muscle Cells Toward an A2B Angiogenic Phenotype". Hypertension. Nov. 2004;44(5):649-54. Epub Sep. 27, 2004. PMID: 15452028 [PubMed—indexed for MEDLINE].
Holgate et al., "Roles of Cysteinyl Leukotrienes in Airway Inflammation, Smooth Muscle Function, and Remodeling". J Allergy Clin Immunol. Jan. 2003;111(1 Suppl):S18-34; discussion S34-6. Review. PMID: 12532084 [PubMed—indexed for MEDLINE].
Hoshino., "Impact of Inhaled Corticosteroids and Leukotrience Receptor Antagonists on Airway Remodeling". Clinical Reviews in Allergy & Immunology, vol. 27 (2004), pp. 59-64.
Jeffery. "Remodeling in Asthma and Chronic Obstructive Lung Disease". Am J. Respir Crit Care Med, vol. 164, pp. S28-S38, 2001. DOI: 10.1164/rccm210606.
Leigh et al., "Is interleukin-13 Critical in Maintaining Airway Hyperresponsiveness in Allergen-Challenged Mice?". Am J Respir Crit Care Med. Oct. 15, 2004;170(8):851-6. Epub Jul. 8, 2004. PMID: 15242841 [PubMed—indexed for MEDLINE].

(Continued)

*Primary Examiner* — Ali Soroush
(74) *Attorney, Agent, or Firm* — Foley & Lardner LLP

(57) ABSTRACT

The present invention relates to methods of preventing airway remodeling using $A_{2B}$ adenosine receptor antagonists. This invention finds utility in the treatment and prevention of asthma, COPD, pulmonary fibrosis, emphysema, and other pulmonary diseases. The invention also relates to pharmaceutical compositions for use in the method.

6 Claims, 8 Drawing Sheets

OTHER PUBLICATIONS

Mann et al., "Airway Effects of Purine Nucleosides and Nucleotides and Release With Bronchial Provocation in Asthma". (1986) J Appl Physiol 61:1667-1676.

Pifferi et al., "Montelukast and Airway Remodeling in Children With Chronic Persistent Asthma: An Open Study". Pediatric Allergy and Immunology 2004I 15L472-473.

Polosa et al., "Evolving Concepts on the Value of Adenosine Hyperres09nsiveness in Asthma and Chronic Objstructive Pulmonary Disease". Thorax 57:649-654, 2002.

Polosa R; "Adenosine-Receptor Subtypes: Their Relevance to Adenosine-Mediated Responses in Asthma and Chronic Obstructive Pulmonary Disease." The European Respiratory Journal: Official Journal of the European Society for Clinical Respiratory Physiology. Aug. 2002, vol. 20, No. 2, Aug. 2002, pp. 488-496.

Ryzhov et al., "Adenosine-Activated Mast Cells Induce IgE Synthesis by B Lymphocytes: An A2B-Mediated Process Involving Th2 Cytokines IL-4 and IL-13 With Implications for Asthma1,2". The Journal of Immunology Jun. 15, 2004;172(12):7726-33. PMID: 15187156 [PubMed—indexed for MEDLINE].

Spicuzza et al., "Research Applications and Implications of Adenosine in Diseased Airways". Trends Pharmacol Sci. Aug. 2003;24(8):409-13. Review. PMID: 12915050 [PubMed—indexed for MEDLINE].

Spicuzza et al., (2003) Curr Opin Allergy Clin Immunol 3:65-69.

Tomita et al., Artificial Neural Network Approach for Selection of Susceptible Single Nucleotide Polymorphisms and Construction of Prediction Model on Childhood Allergic Asthma. BMC Bioinformatics. Sep. 1, 2004;5:120, PMID: 15339344 [PubMed—indexed for MEDLINE].

Zhong Hongyan et al. "Synergy Between A2B Adenosine Receptors and Hypoxia in Activating Human Lung Fibroblasts." American Journal of Respiratory Cell and Molecular Biology. Jan. 2005, vol. 32, No. 1, Jan. 2005, pp. 2-8.

Office Action for U.S. Appl. No. 13/169,834, dated Sep. 6, 2011, 85 pages.

Office Action for U.S. Appl. No. 13/011,446, dated Oct. 17, 2011, 7 pages.

Office Action for U.S. Appl. No. 13/169,834, dated Jan. 19, 2012, 8 pages.

\* cited by examiner

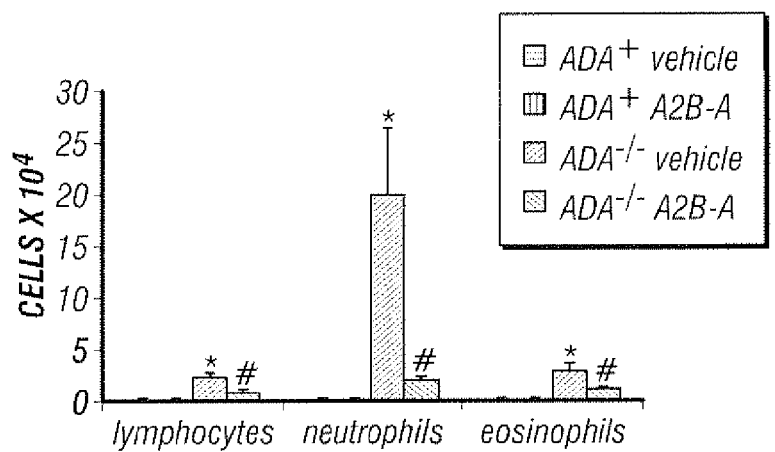
FIG. 2C
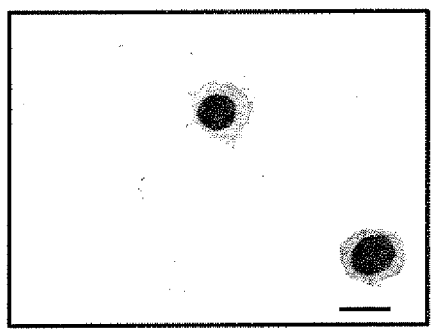 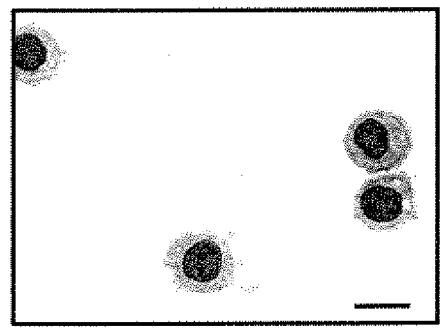
FIG. 3A　　　　　　　　FIG. 3B
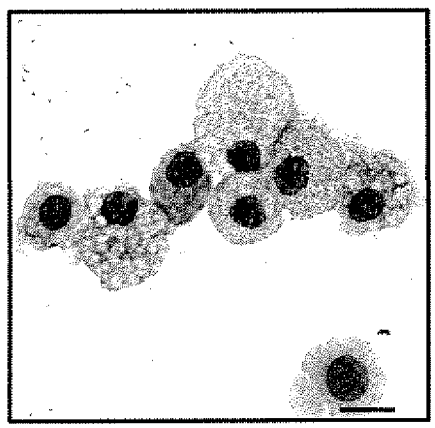 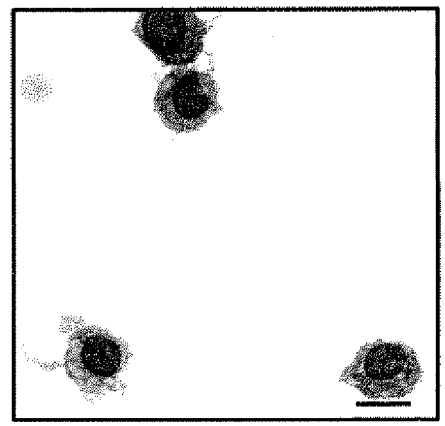
FIG. 3C　　　　　　　　FIG. 3D

METHOD OF PREVENTING AND TREATING AIRWAY REMODELING AND PULMONARY INFLAMMATION USING $A_{2B}$ ADENOSINE RECEPTOR ANTAGONISTS

FIELD OF THE INVENTION

The present invention relates to methods of preventing airway remodeling and/or pulmonary inflammation using $A_{2B}$ adenosine receptor antagonists. This invention finds utility in the treatment and prevention of asthma, COPD, pulmonary fibrosis, emphysema, and other pulmonary diseases. The invention also relates to pharmaceutical compositions for use in the method.

BACKGROUND

According to the Asthma and Allergy Foundation of America and the National Pharmaceutical Council, an estimated 17 million Americans currently suffer from asthma. It is the most common chronic childhood disease, affecting more than one child in 20, nearly 5 million children in all, and it is the only chronic disease, besides AIDS and tuberculosis, with an increasing death rate. Each year over 5,000 Americans die from asthma.

The annual cost of asthma in 1998 was estimated to be $11.3 billion. Direct costs accounted for $7.5 billion and indirect costs were $3.8 billion. Hospitalizations accounted for the single largest portion of the cost and amount to nearly a half million hospitalizations, 1.6 million emergency room visits, and over 10 million office visits. Clearly there is a great need for new methods of treating the condition.

As discussed by Elias et al. (1999), *J. Clin. Inv.*, 104(8):1001-1006, the effects of airway remodeling in the development of asthma were previously unknown as the condition was thought to be an entirely reversible disorder. More recent investigations have revealed, however, that significant airway remodeling occurs during asthma and that the degree of this remodeling is usually proportional to symptom severity. Remodeling typically takes the form of airway wall thickening, the development of subepithelial fibrosis, increased myocyte muscle mass, myofibroblast hyperplasia, and mucus metaplasia. Airway remodeling is also a common factor in the progression of chronic obstructive pulmonary disorder (COPD), and pulmonary fibrosis. Pulmonary inflammation is also a common component in the development of airway remodeling and may be typified by bronchiolitis, alveolitis, and/or vasculitis.

The correlation between airway remodeling and asthma presents a new avenue of asthma research. Recently the ability of cortical steroids and leukotrine receptor antagonists to prevent or treat airway remodeling has been reported (see Hoshino (2004) *Clin Rev Allergy Immunol.* 27(1):59-64). Given the potential negative side effects of long term treatment with cortical steroids and the uncertainties regarding the efficacy of leukotrine receptor antagonists, the exists a strong need for other methods of inhibiting airway remodeling.

Adenosine is known to play a role in asthma and COPD (See, Spicuzza et al. (2003) *TiPS* 24(8):409-4130; Mann et al, (1986) *J Appl Physiol* 61:1667-1676; and Feoktistov et al, (1998) *Trends Pharmacol Sci* 19:148-153.) The clinical evidence supporting the involvement of adenosine includes:

1) Plasma concentrations of adenosine are increased by allergen challenge in asthmatic patients and adenosine levels in the bronchoalveolar lavage fluid are elevated in asthmatic and COPD patients (Driver et al, (1993). *Am Rev Respir Dis* 148:91-97)

2) Adenosine (given as AMP) induces bronchoconstriction in asthmatics but not in normal subjects (Cushley et al, (1983) *Br J Clin Pharmacol* 15:161-165), and it increases the concentrations of mediators released from mast cells, such as histamine, tryptase, LTC4 and PDG2 (Crimi et al, (1997) *Allergy* 52:48-54). The adenosine-induced bronchoconstriction is attenuated by drugs that either inhibit mast cell activation or serve as antagonists to the mediators released from the mast cells. Thus, the potential mechanism of adenosine-induced bronchoconstriction is likely due to its effect on mast cell activation (Polosa et al, (2002) *Thorax* 57:649-654 and Polosa (2002) *Eur Respir J* 20:488-496.).

3) Adenosine has also been shown to induce eosinophilia and inflammation. The overall effects and potential clinical utilities of AMP-challenge are summarized in a recent review article by Spicuzza and Polosa, (2003) *Curr Opin Allergy Clin Immunol* 3:65-69.

Adenosine is a naturally occurring nucleoside, which exerts its biological effects by interacting with a family of adenosine receptors known as $A_1$, $A_{2A}$, $A_{2B}$, and $A_3$, all of which modulate important physiological processes. Of the various receptors, $A_{2B}$ adenosine receptors are believed to be most significantly involved in asthma via their connection to mast cell activation, vasodilation, and regulation of cell growth (See Adenosine $A_{2B}$ Receptors as Therapeutic Targets, *Drug Dev Res* 45:198; Feoktistov et al., *Trends Pharmacol Sci* 19:148-153). Specifically, adenosine $A_{2B}$ receptor antagonists have been shown to affect the activation of mast cell and have thus been implicated in the inhibition of the acute airway hyperresponsiveness. Surprisingly, it has now been found that $A_{2B}$ adenosine receptor antagonists are also useful in the prevention of airway remodeling and pulmonary inflammation.

Accordingly, it is desired to provide a method of preventing airway remodeling and/or pulmonary inflammation by administration of compounds that are potent, fully or partially selective, $A_{2B}$ antagonists, i.e., compounds that inhibit the $A_{2B}$ adenosine receptor.

SUMMARY OF THE INVENTION

In one embodiment of the invention, a method is provided for the treatment and prevention of airway remodeling and/or pulmonary inflammation by administration of a therapeutically effective amount of an $A_{2B}$ receptor antagonist to a mammal that is genetically and/or environmentally predisposed to airway remodeling and pulmonary inflammation.

In another embodiment of the invention, a method is provided for the treatment and prevention of airway remodeling and/or pulmonary inflammation by administration to a mammal that is genetically and/or environmentally predisposed to airway remodeling, a therapeutically effective amount of an $A_{2B}$ receptor antagonist having the structure of Formula I or Formula II:

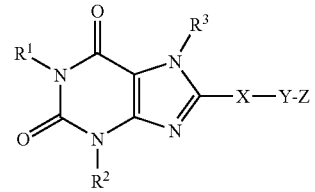

Formula I

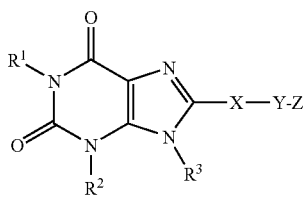

Formula II wherein:
R¹ and R² are independently chosen from hydrogen, optionally substituted alkyl, or a group -D-E, in which D is a covalent bond or alkylene, and E is optionally substituted alkoxy, optionally substituted cycloalkyl, optionally substituted aryl, optionally substituted heteroaryl, optionally substituted heterocyclyl, optionally substituted alkenyl or optionally substituted alkynyl, with the proviso that when D is a covalent bond E cannot be alkoxy;

R³ is hydrogen, optionally substituted alkyl or optionally substituted cycloalkyl;

X is optionally substituted arylene or optionally substituted heteroarylene;

Y is a covalent bond or alkylene in which one carbon atom can be optionally replaced by —O—, —S—, or —NH—, and is optionally substituted by hydroxy, alkoxy, optionally substituted amino, or —COR, in which R is hydroxy, alkoxy or amino; and Z is optionally substituted monocyclic aryl or optionally substituted monocyclic heteroaryl; or Z is hydrogen when X is optionally substituted heteroarylene and Y is a covalent bond.

In yet another embodiment of the invention, pharmaceutical formulations are provided, comprising a therapeutically effective amount of an $A_{2B}$ receptor antagonist, and at least one pharmaceutically acceptable carrier. The formulation is preferably for oral administration.

One preferred group of compounds of Formula I and II are those in which R¹ and R² are independently hydrogen, optionally substituted lower alkyl, or a group -D-E, in which D is a covalent bond or alkylene, and E is optionally substituted phenyl, optionally substituted cycloalkyl, optionally substituted alkenyl, or optionally substituted alkynyl, particularly those in which R³ is hydrogen.

Within this group, a first preferred class of compounds include those in which R¹ and R² are independently lower alkyl optionally substituted by cycloalkyl, preferably n-propyl, and X is optionally substituted phenylene. Within this class, a preferred subclass of compounds are those in which Y is alkylene, including alkylene in which a carbon atom is replaced by oxygen, preferably —O—CH₂—, more especially where the oxygen is the point of attachment to phenylene. Within this subclass, it is preferred that Z is optionally substituted oxadiazole, particularly optionally substituted [1,2,4]-oxadiazol-3-yl, especially [1,2,4]-oxadiazol-3-yl substituted by optionally substituted phenyl or optionally substituted pyridyl.

A second preferred class of compounds include those in which X is optionally substituted 1,4-pyrazolene. Within this class, a preferred subclass of compounds are those in which Y is a covalent bond or alkylene, especially lower alkylene, and Z is hydrogen, optionally substituted phenyl, optionally substituted pyridyl, or optionally substituted oxadiazole. Within this subclass, one preferred embodiment includes compounds in which R¹ is lower alkyl optionally substituted by cycloalkyl, and R² is hydrogen. A more preferred embodiment includes those compounds in which Y is —(CH₂)— or —CH(CH₃)— and Z is optionally substituted phenyl, or Y is —(CH₂)— or —CH(CH₃)— and Z is optionally substituted oxadiazole, particularly 3,5-[1,2,4]-oxadiazole, or Y is —(CH₂)— or —CH(CH₃)— and Z is optionally substituted pyridyl. Within this subclass, also preferred are those compounds in which R¹ and R² are independently lower alkyl optionally substituted by cycloalkyl, especially n-propyl. More preferred are those compounds in which Y is a covalent bond, —(CH₂)— or —CH(CH₃)— and Z is hydrogen, optionally substituted phenyl, or optionally substituted pyridyl, particularly where Y is a covalent bond and Z is hydrogen.

At present, the preferred compounds for use in the invention include, but are not limited to:
1-propyl-8-(1-{[3-(trifluoromethyl)phenyl]methyl}pyrazol-4-yl)-1,3,7-trihydropurine-2,6-dione;
1-propyl-8-[1-benzylpyrazol-4-yl]-1,3,7-trihydropurine-2,6-dione;
1-butyl-8-(1-{[3-fluorophenyl]methyl}pyrazol-4-yl)-1,3,7-trihydropurine-2,6-dione;
1-propyl-8-[1-(phenyl ethyl)pyrazol-4-yl]-1,3,7-trihydropurine-2,6-dione;
8-(1-{[5-(4-chlorophenyl)(1,2,4-oxadiazol-3-yl)]methyl}pyrazol-4-yl)-1-propyl-1,3,7-trihydropurine-2,6-dione;
8-(1-{[5-(4-chlorophenyl)(1,2,4-oxadiazol-3-yl)]methyl}pyrazol-4-yl)-1-butyl-1,3,7-trihydropurine-2,6-dione;
1,3-dipropyl-8-pyrazol-4-yl-1,3,7-trihydropurine-2,6-dione;
1-methyl-3-sec-butyl-8-pyrazol-4-yl-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1,3-dimethyl-8-{1-[(3-fluorophenyl)methyl]pyrazol-4-yl}-1,3,7-trihydropurine-2,6-dione;
3-methyl-1-propyl-8-{1-[(3-trifluoromethylphenyl)methyl]pyrazol-4-yl}-1,3,7-trihydropurine-2,6-dione;
3-ethyl-1-propyl-8-{1-[(3-trifluoromethylphenyl)methyl]pyrazol-4-yl}-1,3,7-trihydropurine-2,6-dione;
1,3-dipropyl-8-(1-{[3-(trifluoromethyl)phenyl]methyl}pyrazol-4-yl)-1,3,7-trihydropurine-2,6-dione;
1,3-dipropyl-8-{1-[(3-fluorophenyl)methyl]pyrazol-4-yl}-1,3,7-trihydropurine-2,6-dione;
1-ethyl-3-methyl-8-{1-[(3-fluorophenyl)methyl]pyrazol-4-yl}-1,3,7-trihydropurine-2,6-dione;
1,3-dipropyl-8-{1-[(2-methoxyphenyl)methyl]pyrazol-4-yl}-1,3,7-trihydropurine-2,6-dione;
1,3-dipropyl-8-(1-{[3-(trifluoromethyl)-phenyl]ethyl}pyrazol-4-yl)-1,3,7-trihydropurine-2,6-dione;
1,3-dipropyl-8-{1-[(4-carboxyphenyl)methyl]pyrazol-4-yl}-1,3,7-trihydropurine-2,6-dione;
2-[4-(2,6-dioxo-1,3-dipropyl(1,3,7-trihydropurin-8-yl))pyrazolyl]-2-phenylacetic acid;
8-{4-[5-(2-methoxyphenyl)-[1,2,4]oxadiazol-3-ylmethoxy]phenyl}-1,3-dipropyl-1,3,7-trihydropurine-2,6-dione;
8-{4-[5-(3-methoxyphenyl)-[1,2,4]oxadiazol-3-ylmethoxy]phenyl}-1,3-dipropyl-1,3,7-trihydropurine-2,6-dione;
8-{4-[5-(4-fluorophenyl)-[1,2,4]oxadiazol-3-ylmethoxy]phenyl}-1,3-dipropyl-1,3,7-trihydropurine-2,6-dione.
1-(cyclopropylmethyl)-8-[1-(2-pyridylmethyl)pyrazol-4-yl]-1,3,7-trihydropurine-2,6-dione;
1-n-butyl-8-[1-(6-trifluoromethylpyridin-3-ylmethyl) pyrazol-4-yl]-1,3,7-trihydropurine-2,6-dione;

8-(1-{[3-(4-chlorophenyl)(1,2,4-oxadiazol-5-yl)]
methyl}pyrazol-4-yl)-1,3-dipropyl-1,3,7-trihydropurine-
2,6-dione;
1,3-dipropyl-8-[1-({5-[4-(trifluoromethyl)phenyl]isoxazol-
3-yl}methyl)pyrazol-4-yl]-1,3,7-trihydropurine-2,6-di-
one;
1,3-dipropyl-8-[1-(2-pyridylmethyl)pyrazol-4-yl]-1,3,7-tri-
hydropurine-2,6-dione;
3-{[4-(2,6-dioxo-1,3-dipropyl-1,3,7-trihydropurin-8-yl)
pyrazolyl]methyl}benzoic acid;
1,3-dipropyl-8-(1-{[6-(trifluoromethyl)(3-pyridyl)]
methyl}pyrazol-4-yl)-1,3,7-trihydropurine-2,6-dione;
1,3-dipropyl-8-{1-[(3-(1H-1,2,3,4-tetraazol-5-yl)phenyl)
methyl]pyrazol-4-yl}-1,3,7-trihydropurine-2,6-dione;
6-{[4-(2,6-dioxo-1,3-dipropyl-1,3,7-trihydropurin-8-yl)
pyrazolyl]methyl}pyridine-2-carboxylic acid;
3-ethyl-1-propyl-8-[1-(2-pyridylmethyl)pyrazol-4-yl]-1,3,
7-trihydropurine-2,6-dione;
8-(1-{[5-(4-chlorophenyl)isoxazol-3-yl]methyl}pyrazol-4-
yl)-3-ethyl-1-propyl-1,3,7-trihydropurine-2,6-dione;
8-(1-{[3-(4-chlorophenyl)(1,2,4-oxadiazol-5-yl)]
methyl}pyrazol-4-yl)-3-ethyl-1-propyl-1,3,7-trihydropu-
rine-2,6-dione;
3-ethyl-1-propyl-8-(1-{[6-(trifluoromethyl)(3-pyridyl)]
methyl}pyrazol-4-yl)-1,3,7-trihydropurine-2,6-dione;
1-(cyclopropylmethyl)-3-ethyl-8-(1-{[6-(trifluoromethyl)
(3-pyridyl)]methyl}pyrazol-4-yl)-1,3,7-trihydropurine-2,
6-dione; and
3-ethyl-1-(2-methylpropyl)-8-(1-{[6-(trifluoromethyl)(3-
pyridyl)]methyl}pyrazol-4-yl)-1,3,7-trihydropurine-2,6-
dione.

SUMMARY OF THE FIGURES

FIG. 3 presents the result of BAL cellularity in ADA−/− mice treated with an adenosine $A_{2B}$ receptor antagonist as described in Example 21. BAL fluid was collected from the lungs of mice and cells were cytospun onto microscope slides and stained with DiffQuick. (A) ADA+ vehicle treated, (B) ADA+ adenosine $A_{2B}$ receptor antagonist treated, (C) ADA−/− vehicle treated, (D) ADA−/− adenosine $A_{2B}$ receptor antagonist treated. Photographs are representative of 6 separate samples of each condition. Scale bar=10 µm.

DETAILED DESCRIPTION OF THE INVENTION

Definitions and General Parameters

Figure 1A:
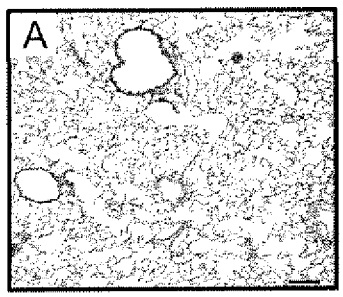
FIG. 1 depicts the differences in pulmonary histopathology in adenosine deaminase (ADA)−/− mice following treatment with adenosine $A_{2B}$ receptor antagonists as described in Example 21. The lungs were collected and processed for histological analysis using H&E staining. (A) Lung from ADA+ vehicle treated mouse. (B) Lung from ADA−/− vehicle treated mouse. (C) Lung from ADA−/− adenosine $A_{2B}$ receptor antagonist treated mouse. (D) Higher magnification section through the lung of an ADA+ vehicle treated mouse. (E) Higher magnification section though the lung of an ADA−/− vehicle treated mouse. (F) Higher magnification section of a lung of an ADA−/− adenosine $A_{2B}$ receptor antagonist treated mouse. Arrows denote alveolar macrophages. Scale bars in A-C=100 µm, scale bars in D-F=10 µm. Sections are representative of 6 different samples from each treatment.
Figure 1B:
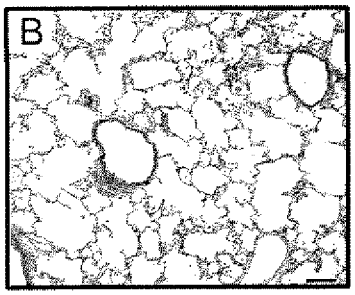
Figure 1C:
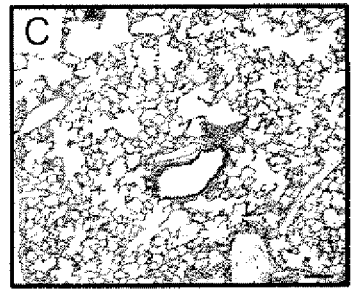
Figure 1D:
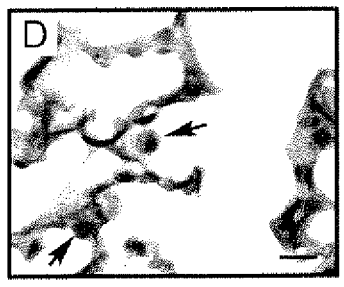

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, preferably 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
2) an alkyl group as defined above that is interrupted by 1-10 atoms independently chosen from oxygen, sulfur and NR$_a$—, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or
3) an alkyl group as defined above that has both 1, 2, 3, 4 or 5 substituents as defined above and is also interrupted by 1-10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, preferably 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1-10 carbon atoms, more preferably 1, 2, 3, 4, 5 or 6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "lower alkylene" refers to a diradical of a branched or unbranched saturated hydrocarbon chain, preferably having from 1, 2, 3, 4, 5, or 6 carbon atoms.

The term "lower alkylene" refers to a diradical of a branched or unbranched saturated hydrocarbon chain, preferably having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or
(2) an alkylene group as defined above that is interrupted by 1-20 atoms independently chosen from oxygen, sulfur and NR$_a$—, where R$_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—CH(NH$_2$)CH$_2$—), methylaminoethylene (—CH(NHMe)CH$_2$—), 2-carboxypropylene isomers(—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$—), 1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio" refers to the group R—S—, where R is as defined for alkoxy.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having 1-6, preferably 1, double bond (vinyl). Preferred alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and S(O)$_n$R, where R is alkyl, aryl, or heteroaryl and n is 0, 1 or 2.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Preferred alkynyl groups include ethynyl,(—C≡CH), propargyl (or prop-1-yn-3-yl, —CH$_2$C≡CH), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and S(O)$_n$R, where R is alkyl, aryl, or heteroaryl and n is 0, 1 or 2.

The term "aminocarbonyl" refers to the group —C(O)NRR where each R is independently hydrogen, alkyl, aryl, heteroaryl, heterocyclyl or where both R groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acylamino" refers to the group —NRC(O)R where each R is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "acyloxy" refers to the groups —O(O)C-alkyl, —O(O)C-cycloalkyl, O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, CF$_3$, amino, substituted amino, cyano, or —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained by the definition for the aryl or arylene substituent, such aryl or arylene groups can optionally be substituted with from 1 to 5 substituents, preferably 1 to 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, carboxyalkyl (for example, benzyloxycarbonyl), aryl, heteroaryl and heterocyclyl provided that both R groups are not hydrogen, or a group —Y—Z, in which Y is optionally substituted alkylene and Z is alkenyl, cycloalkenyl, or alkynyl, Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to carbocyclic groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, bicyclo[2.2.1]heptane, 1,3,3-trimethylbicyclo[2.2.1]kept-2-yl, (2,3,3-trimethylbicyclo[2.2.1]hept-2-yl), or carbocyclic groups to which is fused an aryl group, for example indane, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-oxide and N-alkoxy derivatives of nitrogen containing heteroaryl compounds, for example pyridine-N-oxide derivatives.

The term "heteroarylene" refers to a diradical of a heteroaryl group as defined above. This teen is exemplified by groups such as 2,5-imidazolene, 3,5-[1,2,4]oxadiazolene, 2,4-oxazolene, 1,4-pyrazolene, and the like. For example, 1,4-pyrazolene is:

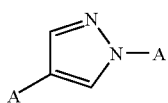

where A represents the point of attachment.

Unless otherwise constrained by the definition for the heteroaryl or heteroarylene substituent, such heteroaryl or heterarylene groups can be optionally substituted with 1 to 5 substituents, preferably 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroaralkyl groups are exemplified by 3-pyridylmethyl, quinolin-8-ylethyl, 4-methoxythiazol-2-ylpropyl, and the like.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthio" refers to the group S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O), in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R$_1$ is substituted alkyl, substituted aryl, or substituted heteroaryl, as defined herein.

The term "keto" refers to a group —C(O)—.

The term "thiocarbonyl" refers to a group —C(S)—.

The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I and Formula II" is intended to encompass the compounds of the invention as disclosed, and the pharmaceutically acceptable salts, pharmaceutically acceptable esters, prodrugs, hydrates and polymorphs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R—S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

"Topical administration" shall be defined as the delivery of the therapeutic agent to the surface of the wound and adjacent epithelium.

"Parenteral administration" is the systemic delivery of the therapeutic agent via injection to the patient.

The term "therapeutically effective amount" refers to that amount of a compound of Formula I that is sufficient to effect treatment, as defined below, when administered to a mammal in need of such treatment. The therapeutically effective amount will vary depending upon the specific activity of the therapeutic agent being used, and the age, physical condition, existence of other disease states, and nutritional status of the patient. Additionally, other medication the patient may be receiving will effect the determination of the therapeutically effective amount of the therapeutic agent to administer.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

The language "genetically and/or environmentally predisposed to airway remodeling and/or pulmonary inflammation" refers to mammals that are susceptible to Examples of such environmental conditions include, but are not limited to, exposure to cigarette smoke and other pollutants, exposure to sprays or chemical agents at work, home, or with hobbies, exposure to common allergens such as dust, grasses, molds, weeds, trees, and animal dander, and exposure to irritants such as asbestos, silica and metal dusts. Examples of genetic predisposition can be evidenced by family history or genetic analysis for suspected mutations in the ADAM33 gene, TLR[4] polymorphisms, IL-3 polymorphisms, CD14 C-159T polymorphisms, and the like. Bioinformatic methods of screening for a genetic predisposition have been presented by Tomita et al. (2004) *BMC Bioinformatics.* 5(1):120. Other conditions and disease states that are known to cause airway remodeling and/or pulmonary inflammation include, but are not limited to, lupus, scleroderma, tuberculosis, and rheumatoid arthritis.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Nomenclature

The naming and numbering of the compounds of the invention is illustrated with a representative compound of Formula I in which $R^1$ is n-propyl, $R^2$ is n-propyl, $R^3$ is hydrogen, X is phenylene, Y is —O—($CH_2$), and Z is 5-(2-methoxyphenyl)-[1,2,4]-oxadiazol-3-yl,

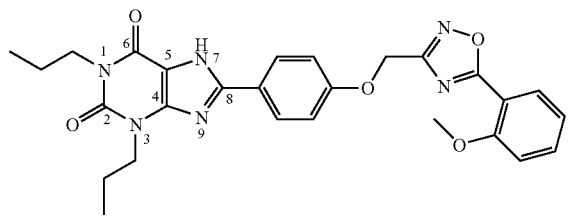 [SMILES: CCCn1c(=O)c2[nH]c(-c3ccc(OCc4noc(-c5ccccc5OC)n4)cc3)nc2n(CCC)c1=O]

which is named:
8-{4-[5-(2-methoxyphenyl)-[1,2,4]-oxadiazol-3-yl-methoxy]-phenyl}-1,3-dipropyl-1,3,7-trihydropurine-2,6-dione.

The Method of the Invention

The present invention relates to methods of preventing airway remodeling and/or pulmonary inflammation by administration of a therapeutically effective amount of a $A_{2B}$ adenosine receptor antagonist to a mammal having a condition that produces or is caused by such airway remodeling. As airway remodeling and pulmonary inflammation are significant components of asthma, pulmonary fibrosis, and COPD, the method of the invention will generally involve administration of an $A_{2B}$ adenosine receptor antagonist to a patient suffering from either asthma, pulmonary fibrosis, and/or COPD.

The $A_{2B}$ adenosine receptor antagonist is administered systemically as an oral formulation but may also be administered directly to the pulmonary tissue via an inhaler. This administration can be as a single dose or as repeated doses given at multiple designated intervals. It will readily be appreciated by those skilled in the art that the preferred dosage regimen will vary with the patient and severity of the condition being treated.

Pharmaceutical Compositions

When selected as the adenosine $A_{2B}$ receptor antagonist, the compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. $17^{th}$ Ed. (1985) and "Modern Pharmaceutics", Marcel Dekker, Inc. $3^{rd}$ Ed. (G. S. Banker & C. T. Rhodes, Eds.).

The $A_{2B}$ Adenosine Receptor Antagonists

Any $A_{2B}$ adenosine receptor antagonist may be used in the method of the invention. Numerous compounds that antagonize the $A_{2B}$ receptor are known in the art, as are methods for determining if a specific compound has such activity. For example, a review article by Feoktistov and Baggioni, ((1997) *Pharmacological Reviews* 49:381-402) reports the binding affinity of eight adenosine receptor agonists and eight antagonists for all four subtypes of adenosine receptors. References cited therein provide detailed descriptions of the procedures used. (Robeva et al, (1996) *J. Drug Dev, Res* 39:243-252; Jacobson et al (1996) *Drug Dev. Res*, 39:289-300; Feoktistov and Baggioni (1993) *Molecular Pharmacology* 43:909-914). Effective methods for determining the binding affinity of a compound for a receptor use a radiolabelled agonist or antagonist and correlation of the binding of that compound to a membrane fraction known to contain that receptor; for example, to determine whether a compound is an $A_{2B}$ antagonist, the membrane fraction would contain the $A_{2B}$ adenosine receptor. Another particularly effective procedure for determining whether a compound is an $A_{2B}$ antagonist is reported in U.S. Pat. No. 5,854,081.

Compounds selective for the $A_{2B}$ receptor subtype are therefore preferred for the present methods. An example, but not a limitation, of such a compound is 3-n-propylxanthine (enprofylline). Suitable compounds are also disclosed in U.S. Pat. No. 6,545,002. Compounds that antagonize other receptors in addition to the $A_{2B}$ receptor are also suitable for use in the present invention. One example of such a compound is 1,3-dipropyl-8-(p-acrylic)phenylxanthine.

One particularly preferred class of $A_{2B}$ adenosine receptor antagonists are those disclosed in copending and commonly assigned U.S. Pat. No. 6,825,349 and in copending and commonly assigned U.S. patent application Ser. No. 10/719,102, which published as U.S. Patent Application Publication No. 20040176399. The compounds disclosed in that application have the structure of Formula I and Formula II as presented in the Summary of the Invention above and can be synthesized as described in the references or as detailed below.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents, and the reactions are carried out under an inert gas, preferably nitrogen.

The term "q.s." means adding a quantity sufficient to achieve a stated function, e.g., to bring a solution to the desired volume (i.e., 100%).

Synthesis of the Compounds of Formula I and II

One preferred method of preparing compounds of Formula I or II where $R^3$ is hydrogen is shown in Reaction Scheme I.

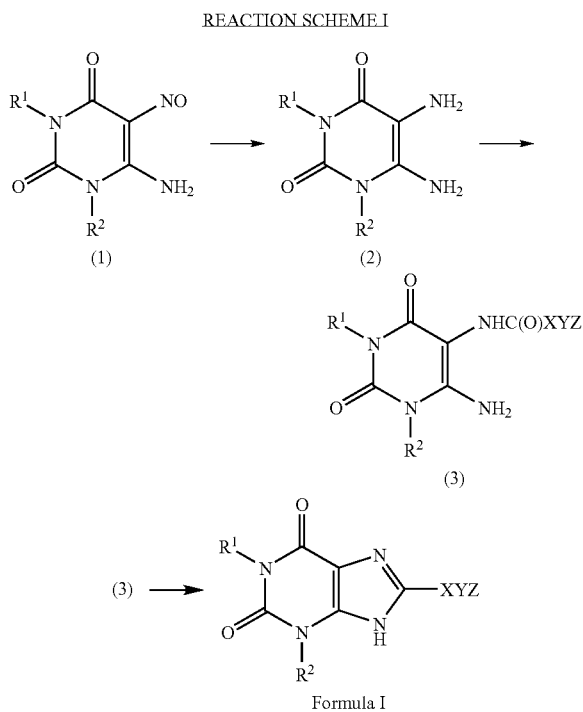

Step 1—Preparation of Formula (2)

The compound of formula (2) is made from the compound of formula (1) by a reduction step. Conventional reducing techniques may be used, for example using sodium dithionite in aqueous ammonia solution; preferably, reduction is carried out with hydrogen and a metal catalyst. The reaction is carried out at in an inert solvent, for example methanol, in the presence of a catalyst, for example 10% palladium on carbon catalyst, under an atmosphere of hydrogen, preferably under pressure, for example at about 30 psi, for about 2 hours. When the reaction is substantially complete, the product of formula (2) is isolated by conventional means to provide a compound of formula (2).

Step 2—Preparation of Formula (3)

The compound of formula (2) is then reacted with a carboxylic acid of the formula Z—Y—X—CO$_2$H in the presence of a carbodiimide, for example 1-(3-dimethylaminopropyl)-3-ethylcarbodiimide hydrochloride. The reaction is conducted in a protic solvent, for example methanol, ethanol, propanol, and the like, preferably methanol, at a temperature of about 20-30° C., preferably about room temperature, for about 12-48 hours, preferably about 16 hours. When the reaction is substantially complete, the product of formula (3) is isolated conventionally, for example by removal of the solvent under reduced pressure, and washing the product. Alternatively, the next step can be carried out without any further purification.

Alternative Preparation of a Compound of Formula (3)

Alternatively, the carboxylic acid of the formula Z—Y—X—CO$_2$H is first converted to an acid halide of the formula Z—Y—X—C(O)L, where L is chloro or bromo, by reacting with a halogenating agent, for example thionyl chloride or thionyl bromide, preferably thiony chloride. Alternatively, oxalyl chloride, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product is then reacted with a compound of formula (2) in an inert solvent, for example acetonitrile, in the presence of a tertiary base, for example triethylamine. The reaction is conducted at an initial temperature of about 0C, and then allowed to warm to 20-30° C., preferably about room temperature, for about 12-48 hours, preferably about 16 hours. When the reaction is substantially complete, the product of formula (3) is isolated conventionally, for example by diluting the reaction mixture with water, filtering off the product, and washing the product with water followed by ether.

Step 3—Preparation of Formula I

The compound of formula (3) is then converted into a compound of Formula I by a cyclization reaction. The reaction is conducted in a protic solvent, for example methanol, ethanol, propanol, and the like, preferably methanol, in the presence of a base, for example potassium hydroxide, sodium hydroxide, sodium methoxide, sodium ethoxide, potassium t-butoxide, preferably aqueous sodium hydroxide, at a temperature of about 50-80° C., preferably about 80° C., for about 1-8 hours, preferably about 3 hours. When the reaction is substantially complete, the product of Formula I is isolated conventionally, for example by removal of the solvent under reduced pressure, acidifying the residue with an aqueous acid, filtering off the product, then washing and drying the product.

The compound of formula (1) may be prepared by various methods. One preferred method is shown in Reaction Scheme II.

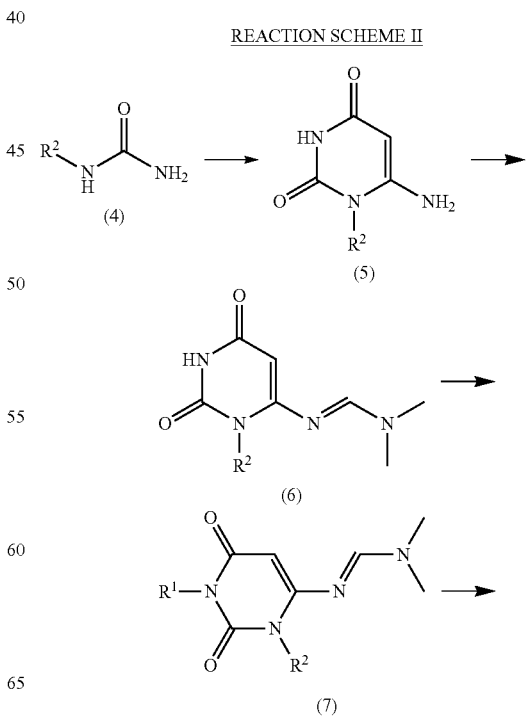

-continued

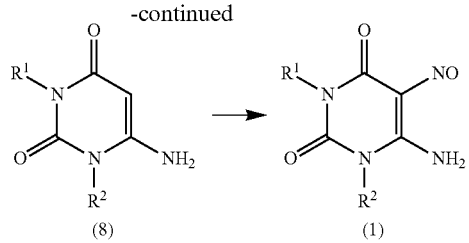

Step 1—Preparation of Formula (5)

The compound of formula (4) is either commercially available or prepared by means well known in the art. It is reacted with ethyl cyanoacetate in a protic solvent, for example ethanol, in the presence of a strong base, for example sodium ethoxide. The reaction is carried out at about reflux temperature, for about 4 to about 24 hours. When the reaction is substantially complete, the compound of formula (5) thus produced is isolated conventionally.

Step 2 and 3—Preparation of Formula (7)

The compound of formula (5) is reacted with the dimethylacetal of N,N-dimethylformamide in a polar solvent, for example N,N-dimethylformamide. The reaction is carried out at about 40° C., for about 1 hour. When the reaction is substantially complete, the compound of formula (6) thus produced is reacted with a compound of formula R¹Hal, where Hal is chloro, bromo, or iodo, in the presence of a base, for example potassium carbonate. The reaction is carried out at about 80° C., for about 4-24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1-3 days. When the reaction is substantially complete, the product of formula (8) is isolated conventionally, for example by chromatography over a silica gel column, eluting, for example, with a mixture of dichloromethane/methanol.

Step 5—Preparation of Formula (1)

The compound of formula (8) is then mixed with sodium nitrite in an aqueous acidic solvent, preferably acetic acid and water, for example 50% acetic acid/water. The reaction is carried out at a temperature of about 50-90° C., preferably about 70° C., for about 1 hour. When the reaction is substantially complete, the product of formula (1) is isolated by conventional means.

Alternatively, the reaction may be conducted in an aqueous solvent, for example dimethylformamide and water, and reacted with a strong acid, for example hydrochloric acid.

A compound of formula (8) can be prepared from a compound of formula (10) using a similar method, as shown in Reaction Scheme IIA.

REACTION SCHEME IIA

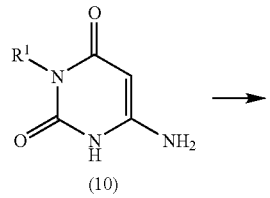

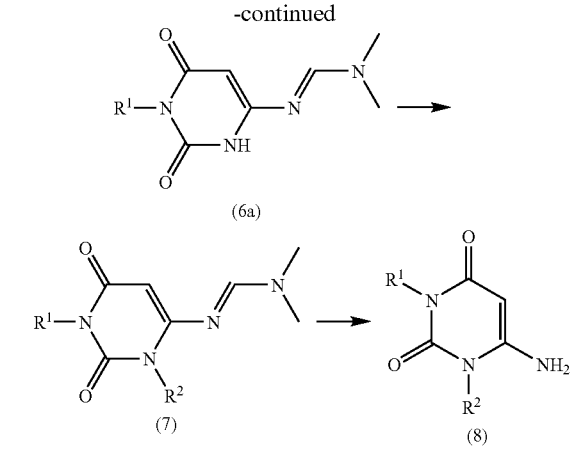

Step 2 and 3—Preparation of Formula (7)

The compound of formula (10) is reacted with the dimethylacetal of N,N-dimethylformamide in a polar solvent, for example N,N-dimethylfounamide. The reaction is carried out at about 40° C., for about 1 hour. When the reaction is substantially complete, the compound of formula (6a) thus produced is reacted with a compound of formula R²Hal, where Hal is chloro, bromo, or iodo, in the presence of a base, for example potassium carbonate. The reaction is carried out at about 80° C., for about 4-24 hour. When the reaction is substantially complete, the product of formula (7) is isolated conventionally, for example by evaporation of the solvents under reduced pressure, and the residue is used in the next reaction with no further purification.

Step 4—Preparation of Formula (8)

The compound of formula (7) is reacted with aqueous ammonia in a polar solvent, for example suspended in methanol. The reaction is carried out at about room temperature, for about 1-3 days. When the reaction is substantially complete, the product of formula (8) is isolated conventionally, for example by chromatography over a silica gel column, eluting, for example, with a mixture of dichloromethane/methanol.

The compound of formula (3) may also be prepared by various methods. One preferred method is shown in Reaction Scheme III.

REACTION SCHEME III

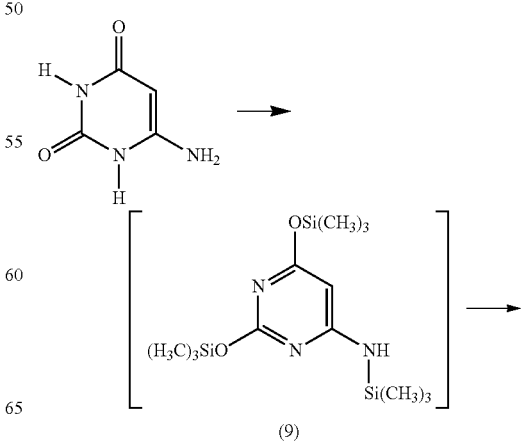

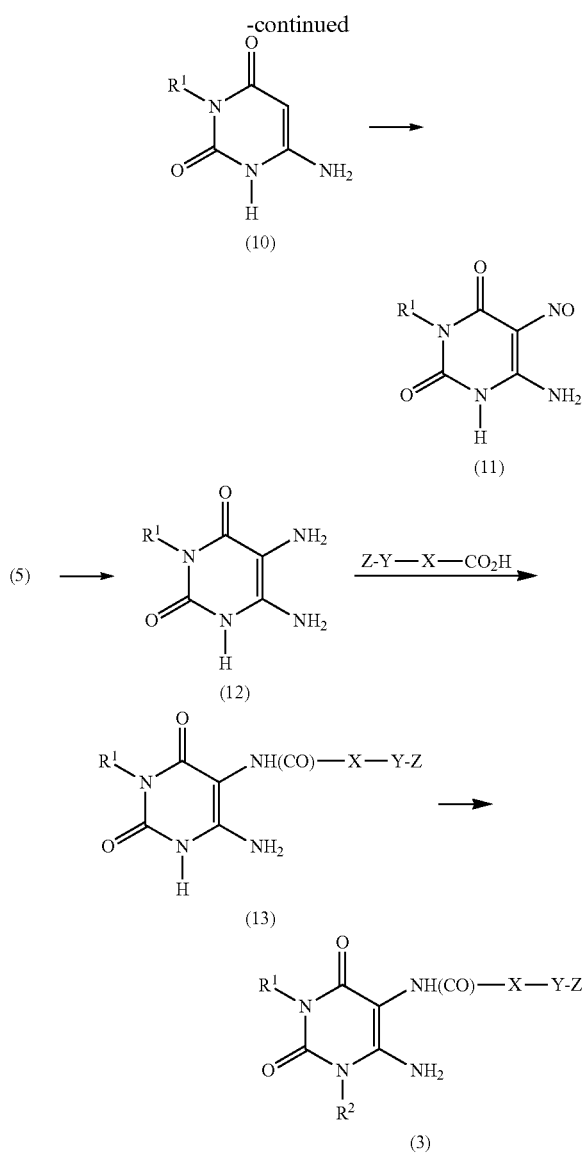

Step 1—Preparation of Formula (10)

The commercially available compound 6-aminouracil is first silylated, for example by reaction with excess hexamethyldisilazane as a solvent in the presence of a catalyst, for example ammonium sulfate. The reaction is carried out at about reflux temperature, for about 1-10 hours. When the reaction is substantially complete, the silylated compound thus produced is isolated conventionally, and then reacted with a compound of formula $R^1Hal$, where Hal is chloro, bromo, or iodo, preferably in the absence of a solvent. The reaction is carried out at about reflux, for about 4-48 hours, preferably about 12-16 hours. When the reaction is substantially complete, the product of formula (10) is isolated by conventional means.

Step 2—Preparation of Formula (11)

The compound of formula (10) is then dissolved in an aqueous acid, for example aqueous acetic acid, and reacted with sodium nitrite. The reaction is carried out at a temperature of about 20-50° C., preferably about 30° C., over about 30 minutes. When the reaction is substantially complete, the product of formula (11) is isolated by conventional means, for example by filtration.

Step 3—Preparation of Formula (12)

The compound of formula (11) is then reduced to a diamino derivative. In general, the compound of formula (11) is dissolved in aqueous ammonia, and then a reducing agent, for example sodium hydrosulfite, added. The reaction is conducted at a temperature of about 70° C. When the reaction is substantially complete, the product of formula (12) is isolated conventionally, for example by filtration of the cooled reaction mixture.

Step 4—Preparation of Formula (13)

The compound of formula (12) is then reacted with a carboxylic acid of the formula Z—Y—X—$CO_2H$ in the presence of a carbodiimide, for example 1-(3-dimethylaminopropyl)-3-ethylcarbodiimide hydrochloride. The reaction is conducted at a temperature of about 20-30° C., for about 12-48 hours. When the reaction is substantially complete, the product of formula (13) is isolated conventionally, for example by filtration of the cooled reaction mixture.

Alternatively, the carboxylic acid of the formula Z—Y—X—$CO_2H$ is converted to an acid halide of the formula Z—Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product of the formula Z—Y—X—C(O)L is then reacted with a compound of formula (12) in an inert solvent, for example acetonitrile, in the presence of a tertiary base, for example triethylamine. The reaction is conducted at an initial temperature of about 0C, and then allowed to warm to 20-30° C., preferably about room temperature, for about 12-48 hours, preferably about 16 hours. When the reaction is substantially complete, the product of formula (13) is isolated conventionally, for example by diluting the reaction mixture with water, filtering off the product, and washing the product with water followed by ether.

Step 5—Preparation of Formula (3)

The compound of formula (13) is reacted with a compound of formula $R^2Hal$, where Hal is chloro, bromo, or iodo, in the presence of a base, for example potassium carbonate. The reaction is carried out at about room temperature, for about 4-24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

Another method of preparing a compound of formula (3) is shown in Reaction Scheme IV.

REACTION SCHEME IV

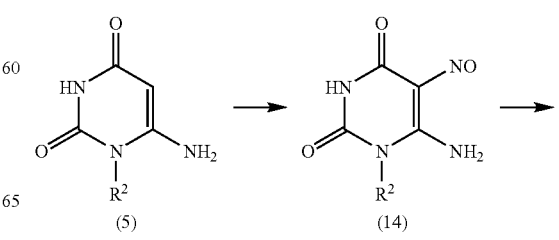

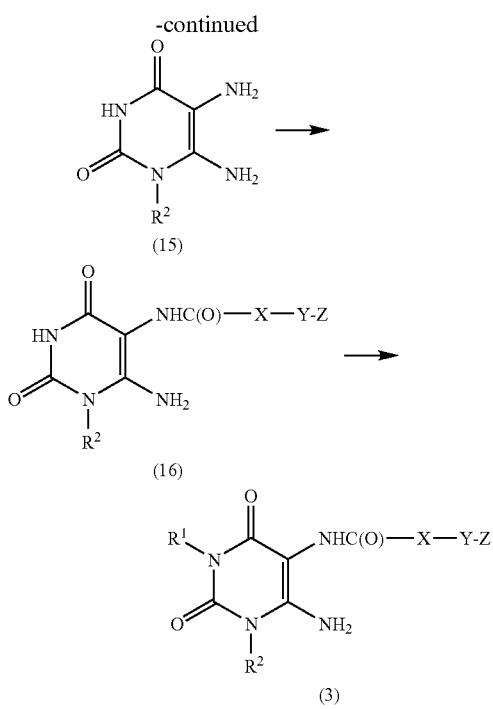

Step 1—Preparation of Formula (14)

The compound of formula (5) is then mixed with sodium nitrite in an aqueous acidic solvent, preferably acetic acid and water, for example 50% acetic acid/water. The reaction is carried out at a temperature of about 50-90° C., preferably about 70° C., for about 1 hour. When the reaction is substantially complete, the product of formula (14) is isolated by conventional means.

Alternatively, the reaction may be conducted in an aqueous solvent, for example dimethylformamide and water, and reacted with a strong acid, for example hydrochloric acid.

Step 3—Preparation of Formula (15)

The compound of formula (14) is then reduced to a diamino derivative. In general, the compound of formula (14) is dissolved in aqueous ammonia, and then a reducing agent, for example sodium hydrosulfite, added. The reaction is conducted at a temperature of about 70° C. When the reaction is substantially complete, the product of formula (15) is isolated conventionally, for example by filtration of the cooled reaction mixture.

Step 4—Preparation of Formula (16)

The compound of formula (15) is then reacted with a carboxylic acid of the formula Z—Y—X—CO$_2$H in the presence of a carbodiimide, for example 1-(3-dimethylaminopropyl)-3-ethylcarbodiimide hydrochloride. The reaction is conducted at a temperature of about 20-30° C., for about 12-48 hours, in an inert solvent, for example methanol. When the reaction is substantially complete, the product of formula (16) is isolated conventionally, for example by filtration of the cooled reaction mixture.

Alternatively, the carboxylic acid of the formula Z—Y—X—CO$_2$H is converted to an acid halide of the formula Z—Y—X—C(O)L, where L is chloro or bromo, by reacting with a halogenating agent, for example thionyl chloride or thionyl bromide; alternatively, phosphorus pentachloride or phosphorus oxychloride may be used. The reaction is preferably conducted in the absence of a solvent, using excess halogenating agent, for example at a temperature of about 60-80° C., preferably about 70° C., for about 1-8 hours, preferably about 4 hours. When the reaction is substantially complete, the product of formula Z—Y—X—C(O)L is isolated conventionally, for example by removal of the excess halogenating agent under reduced pressure.

The product of the formula Z—Y—X—C(O)L is then reacted with a compound of formula (15) in an inert solvent, for example acetonitrile, in the presence of a tertiary base, for example triethylamine. The reaction is conducted at an initial temperature of about 0C, and then allowed to warm to 20-30° C., preferably about room temperature, for about 12-48 hours, preferably about 16 hours. When the reaction is substantially complete, the product of formula (16) is isolated conventionally, for example by diluting the reaction mixture with water, filtering off the product, and washing the product with water followed by ether.

Step 5—Preparation of Formula (3)

The compound of formula (16) is reacted with a compound of formula R$^1$ Hal, where Hal is chloro, bromo, or iodo, in the presence of a base, for example potassium carbonate. The reaction is carried out at about 80° C., for about 4-24 hour, preferably about 16 hours. When the reaction is substantially complete, the product of formula (3) is isolated conventionally, for example by evaporation of the solvents under reduced pressure, and the residue may be purified conventionally, or may be used in the next reaction with no further purification.

An example of a synthesis of a compound of Z—Y—X—CO$_2$H in which X is pyrazol-1,4-yl, Y is methylene, and Z is 3-trifluoromethylphenyl, is shown in Reaction Scheme V.

REACTION SCHEME V

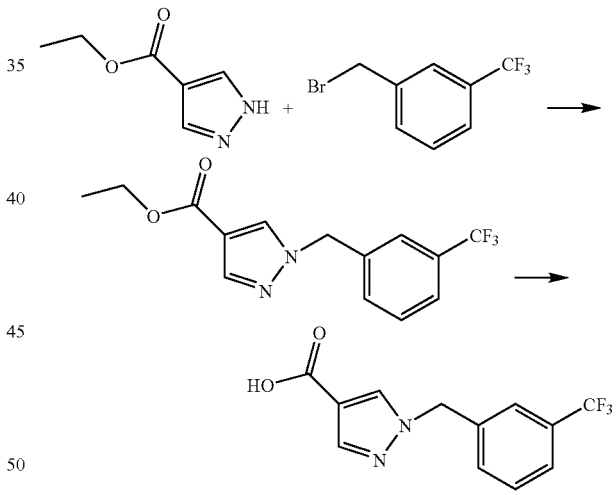

Ethyl pyrazole-4-carboxylate is reacted with 1-(bromomethyl)-3-(trifluoromethyl)benzene in acetone in the presence of potassium carbonate. The product, ethyl 1-{[3-(trifluoromethyl)phenyl]methyl}pyrazole-4-carboxylate, is then hydrolyzed with potassium hydroxide in methanol, to provide 1-{[3-(trifluoromethyl)phenyl]methyl}pyrazole-4-carboxylic acid.

Utility Testing and Administration

General Utility

The method and pharmaceutical compositions of the invention are effective in the prevention of airway remodeling and/or pulmonary inflammation in a mammal that is predisposed to airway remodeling and/or pulmonary inflammation.

The predisposition may be due to genetic abnormalities, disease states, and/or environmental conditions that have been shown to induce airway remodeling and/or pulmonary inflammation.

Testing

Activity testing is conducted as described in those patents and patent applications referenced above, and in the Examples below, and by methods apparent to one skilled in the art.

Administration

The compounds of Formula I may be administered in either single or multiple doses by any of the accepted modes of administration of agents having similar utilities, for example as described in those patents and patent applications incorporated by reference, including buccal, intranasal, intra-arterial injection, intravenously, intraperitoneally, parenterally, intramuscularly, subcutaneously, orally, or as an inhalant.

Oral administration is the preferred route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Adenosine $A_{2B}$ receptor antagonists such as the compounds of Formula I are effective over a wide dosage range and is generally administered in a pharmaceutically effective amount. Typically, for oral administration, each dosage unit contains from 1 mg to 2 g of an adenosine $A_{2B}$ receptor antagonist, more commonly from 1 to 700 mg, and for parenteral administration, from 1 to 700 mg of an adenosine $A_{2B}$ receptor antagonist, more commonly about 2 to 200 mg. It will be understood, however, that the amount of the adenosine $A_{2B}$ receptor antagonist actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine, Solution, suspension, or powder compositions may be administered, preferably orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (5)

A. Preparation of a Compound of Formula (5) in which $R^2$ is Ethyl

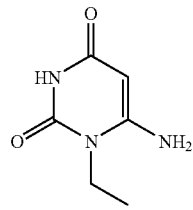

A solution of sodium ethoxide was prepared from sodium (4.8 g, 226 mmol) and dry ethanol (150 ml). To this solution was added amino-N-ethylamide (10 g, 113 in mol) and ethyl cyanoacetate (12.8 g, 113 mmol). This reaction mixture was stirred at reflux for 6 hours, cooled, and solvent removed from the reaction mixture under reduced pressure. The residue was dissolved in water (50 ml), and the pH adjusted to 7 with hydrochloric acid. The mixture was allowed to stand overnight at 0° C., and the precipitate filtered off, washed with water and air-dried, to provide 6-amino-1-ethyl-1,3-dihydropyrimidine-2,4-dione, a compound of formula (5).

$^1$H-NMR (DMSO-d6) δ 10.29 (s, 1H), 6.79 (s, 2H), 4.51 (s, 1H), 3.74-3.79 (m, 2H), 1.07 (t, 3H, J=7.03 Hz); MS m/z 155.98 (M$^+$), 177.99 (M$^+$+Na)

B. Preparation of a Compound of Formula (5) in which $R^2$ is Methyl

Similarly, following the procedure of Example 1A, but replacing amino-N-ethylamide with amino-N-methylamide, 6-amino-1-methyl-1,3-dihydropyrimidine-2,4-dione was prepared.

C. Preparation of a Compound of Formula (5) varying $R^2$

Similarly, following the procedure of Example 1A, but replacing amino-N-ethylamide with other compounds of formula (4), other compounds of formula (5) are prepared.

EXAMPLE 2

Preparation of a Compound of Formula (6)

A. Preparation of a Compound of Formula (6) in which $R^2$ is Ethyl

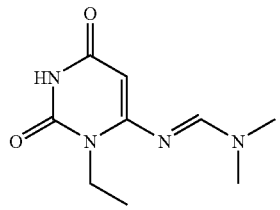

A suspension of 6-amino-1-ethyl-1,3-dihydropyrimidine-2,4-dione (0.77 g, 5 mmol) in anhydrous N,N-dimethylacetamide (25 ml) and N,N-dimethylformamide dimethylacetal (2.7 ml, 20 mmol) and was warmed at 40° C. for 90 minutes. Solvent was then removed under reduced pressure, and the residue triturated with ethanol, filtered, and washed with ethanol, to provide 6-[2-(dimethylamino)-1-azavinyl]-1-ethyl-1,3-dihydropyrimidine-2,4-dione, a compound of formula (6).

$^1$H-NMR (DMSO-d6) δ 10.62 (s, 1H), 8.08 (s, 1H), 4.99 (s, 1H), 3.88-3.95 (m, 2H), 3.13 (s, 3H), 2.99 (s, 3H), 1.07 (t, 3H, J=7.03 Hz); MS m/z 210.86 (M$^+$), 232.87 (M$^+$+Na)

B. Preparation of a Compound of Formula (6) in which $R^2$ is Methyl

Similarly, following the procedure of Example 2A, but replacing 6-amino-1-ethyl-1,3-dihydropyrimidine-2,4-dione with 6-amino-1-methyl-1,3-dihydropyrimidine-2,4-dione, 6-[2-(dimethylamino)-1-azavinyl]-1-methyl-1,3-dihydropyrimidine-2,4-dione was prepared.

C. Preparation of a Compound of Formula (6) varying $R^2$

Similarly, following the procedure of Example 2A, but replacing 6-amino-1-ethyl-1,3-dihydropyrimidine-2,4-dione with other compounds of formula (5), other compounds of formula (6) are prepared.

EXAMPLE 3

Preparation of a Compound of Formula (7)

A. Preparation of a Compound of Formula (7) in which $R^1$ is n-Propyl and $R^2$ is Ethyl

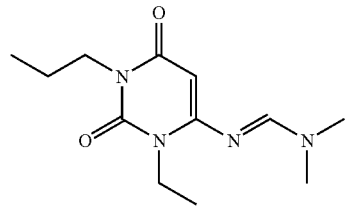 [SMILES: CCCn1c(=O)cc(/N=C/N(C)C)n(CC)c1=O]

A mixture of a solution of 6-[2-(dimethylamino)-1-azavinyl]-1-ethyl-1,3-dihydropyrimidine-2,4-dione (1.5 g, 7.1 mmol) in dimethylformamide (25 ml), potassium carbonate (1.5 g, 11 mmol) and n-propyl iodide (1.54 g, 11 mmol) was stirred at 80° C. for 5 hours. The reaction mixture was cooled to room temperature, filtered, the solvents were evaporated and the product of formula (7), 6-[2-(dimethylamino)-1-azavinyl]-1-ethyl-3-propyl-1,3-dihydropyrimidine-2,4-dione, was used as such in the next reaction.

B. Preparation of a Compound of Formula (7), varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), the following compounds of formula (7) were prepared:

6-[2-(dimethylamino)-1-azavinyl]-1-methyl-3-propyl-1,3-dihydropyrimidine-2,4-dione.

6-[2-(dimethylamino)-1-azavinyl]-1-methyl-3-cyclopropyl-methyl-1,3-dihydropyrimidine-2,4-dione;

6-[2-(dimethylamino)-1-azavinyl]-1-ethyl-3-cyclopropylmethyl-1,3-dihydropyrimidine-2,4-dione;

6-[2-(dimethylamino)-1-azavinyl]-1-methyl-3-(2-methylpropyl)-1,3-dihydropyrimidine-2,4-dione; and 6-[2-(dimethylamino)-1-azavinyl]-1-ethyl-3-(2-methylpropyl)-1,3-dihydropyrimidine-2,4-dione.

C. Preparation of a Compound of Formula (7), varying $R^1$ and $R^2$

Similarly, following the procedure of Example 3A, but replacing 6-[2-(dimethylamino)-1-azavinyl]-1-ethyl-1,3-dihydropyrimidine-2,4-dione with other compounds of formula (6), other compounds of formula (7) are prepared.

EXAMPLE 4

Preparation of a Compound of Formula (8)

A. Preparation of a Compound of Formula (8) in which $R^1$ is n-Propyl and $R^2$ is Ethyl

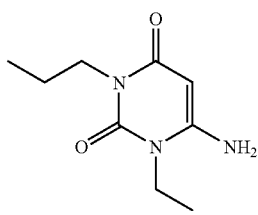

A solution of 6-[2-(dimethylamino)-1-azavinyl]-1-ethyl-3-propyl-1,3-dihydropyrimidine-2,4-dione (2.1 g) was dissolved in a mixture of methanol (10 ml) and 28% aqueous ammonia solution (20 ml), and stirred for 72 hours at room temperature. Solvent was then removed under reduced pressure, and the residue purified by chromatography on a silica gel column, eluting with a mixture of dichloromethane/methanol (15/1), to provide 6-amino-1-ethyl-3-propyl-1,3-dihydropyrimidine-2,4-dione, a compound of formula (8).

$^1$H-NMR (DMSO-d6) δ 6.80 (s, 2H), 4.64 (s, 1H), 3.79-3.84 (m, 2H), 3.63-3.67 (m, 2H), 1.41-1.51 (m, 2H), 1.09 (t, 3H, J=7.03 Hz), 0.80 (t, 3H, J=7.42 Hz); MS m/z 197.82 (M$^+$)

B. Preparation of a Compound of Formula (8), varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), the following compounds of formula (8) were prepared:

6-amino-1-methyl-3-propyl-1,3-dihydropyrimidine-2,4-dione;

6-amino-1-methyl-3-cyclopropylmethyl-1,3-dihydropyrimidine-2,4-dione;

6-amino-1-ethyl-3-cyclopropylmethyl-1,3-dihydropyrimidine-2,4-dione;

6-amino-1-methyl-3-(2-methylpropyl)-1,3-dihydropyrimidine-2,4-dione; and 6-amino-1-ethyl-3-(2-methylpropyl)-1,3-dihydropyrimidine-2,4-dione.

C. Preparation of a Compound of Formula (7) varying $R^1$ and $R^2$

Similarly, following the procedure of Example 4A, but replacing 6-[2-(dimethylamino)-1-azavinyl]-1-ethyl-3-propyl-1,3-dihydropyrimidine-2,4-dione with other compounds of formula (7), other compounds of formula (8) are prepared.

EXAMPLE 5

Preparation of a Compound of Formula (1)

A. Preparation of a Compound of Formula (1) in which $R^1$ is n-Propyl and $R^2$ is Ethyl

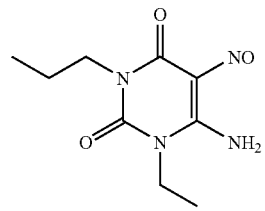

To a solution of 6-amino-1-ethyl-3-propyl-1,3-dihydropyrimidine-2,4-dione (1.4 g, 7.1 mmol) in a mixture of 50% acetic acid/water (35 ml) was added sodium nitrite (2 g, 28.4 mmol) in portions over a period of 10 minutes. The mixture was stirred at 70° C. for 1 hour, then the reaction mixture concentrated to a low volume under reduced pressure. The solid was filtered off, and washed with water, to provide 6-amino-1-ethyl-5-nitroso-3-propyl-1,3-dihydropyrimidine-2,4-dione, a compound of formula (1).

MS m/z 227.05 (M$^+$), 249.08 (M$^+$+Na)

B. Preparation of a Compound of Formula (1), varying $R^1$ and $R^2$

Similarly, following the procedure of Example 5A, but replacing 6-amino-1-ethyl-3-propyl-1,3-dihydropyrimidine-2,4-dione with other compounds of formula (8), the following compounds of formula (1) were prepared:

6-amino-1-methyl-5-nitroso-3-propyl-1,3-dihydropyrimidine-2,4-dione;

6-amino-1-methyl-3-cyclopropylmethyl-5-nitroso-1,3-dihydropyrimidine-2,4-dione;

6-amino-1-ethyl-3-cyclopropylmethyl-5-nitroso-1,3-dihydropyrimidine-2,4-dione;

6-amino-1-methyl-3-(2-methylpropyl)-5-nitroso-1,3-dihydropyrimidine-2,4-dione; and 6-amino-1-ethyl-3-(2-methylpropyl)-5-nitroso-1,3-dihydropyrimidine-2,4-dione.

C. Preparation of a Compound of Formula (1) varying $R^1$ and $R^2$

Similarly, following the procedure of Example 5A, but replacing 6-amino-1-ethyl-3-propyl-1,3-dihydropyrimidine-2,4-dione with other compounds of formula (8), other compounds of formula (1) are prepared.

EXAMPLE 6

Preparation of a Compound of Formula (2)

A. Preparation of a Compound of Formula (2) in which $R^1$ is n-Propyl and $R^2$ is Ethyl

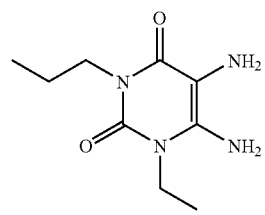

To a solution of 6-amino-1-ethyl-5-nitroso-3-propyl-1,3-dihydropyrimidine-2,4-dione (300 mg) in methanol (10 ml) was added 10% palladium on carbon catalyst (50 mg), and the mixture was hydrogenated under hydrogen at 30 psi for 2 hours. The mixture was filtered through celite, and solvent was removed from the filtrate under reduced pressure, to provide 5,6-diamino-1-ethyl-3-propyl-1,3-dihydropyrimidine-2,4-dione, a compound of formula (2).

MS m/z 213.03 (M+), 235.06 (M++Na)

B. Preparation of a Compound of Formula (2), varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), the following compounds of formula (2) were prepared:

5,6-diamino-1-methyl-3-propyl-1,3-dihydropyrimidine-2,4-dione;
5,6-diamino-1-methyl-3-cyclopropylmethyl-1,3-dihydropyrimidine-2,4-dione;
5,6-diamino-1-ethyl-3-cyclopropylmethyl-1,3-dihydropyrimidine-2,4-dione;
5,6-amino-1-methyl-3-(2-methylpropyl)-1,3-dihydropyrimidine-2,4-dione; and
5,6-diamino-1-ethyl-3-(2-methylpropyl)-1,3-dihydropyrimidine-2,4-dione.

C. Preparation of a Compound of Formula (2) varying $R^1$ and $R^2$

Similarly, following the procedure of Example 6A, but replacing 6-amino-1-ethyl-5-nitroso-3-propyl-1,3-dihydropyrimidine-2,4-dione with other compounds of formula (1), other compounds of formula (2) are prepared.

EXAMPLE 7

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

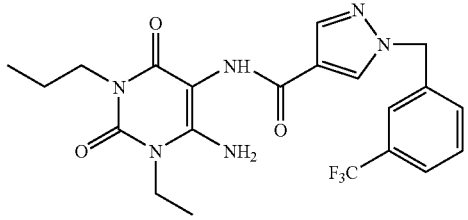 [SMILES: CCCn1c(=O)c(NC(=O)c2cnn(Cc3cccc(C(F)(F)F)c3)c2)c(N)n(CC)c1=O]

To a mixture of 5,6-diamino-1-ethyl-3-propyl-1,3-dihydropyrimidine-2,4-dione (100 mg, 0.47 mmol) and 1-{[3-(trifluoromethyl)phenyl]methyl}pyrazole-4-carboxylic acid (0.151 g, 0.56 mmol) in methanol (10 ml) was added 1-(3-dimethylaminopropyl)-3-ethylcarbodiimide hydrochloride (0.135 g, 0.7 mmol), and the reaction mixture was stirred overnight at room temperature. The solvent was removed under reduced pressure, and the residue purified using Bistag, eluting with 10% methanol/methylene chloride, to provide N-(6-amino-1-ethyl-2,4-dioxo-3-propyl(1,3-dihydropyrimidin-5-yl))(1-{[3-(trifluoromethyl)phenyl]methyl}-pyrazol-4-yl)carboxamide.

¹H-NMR (DMSO-d6) δ 8.59 (s, 1H), 8.02 (s, 1H), 7.59-7.71 (m, 4H), 6.71 (s, 2H), 5.51 (s, 2H), 3.91-3.96 (m, 2H), 3.70-3.75 (m, 2H), 1.47-1.55 (m, 2H), 1.14 (t, 3H, J=7.03 Hz), 0.85 (t, 3H, J=7.42 Hz).

B. Preparation of a Compound of Formula (3), varying $R^1$, $R^2$, X, Y, and Z

Similarly, following the procedure of Example 7A or 7B, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z—Y—X—CO₂H, the following compounds of formula (3) were prepared:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;
N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;
N-(6-amino-1-ethyl-2,4-dioxo-3-cyclopropylmethyl(1,3-dihydropyrimidin-5-yl))(1-{[3-(trifluoromethyl)phenyl]methyl}-pyrazol-4-yl)carboxamide;
N-(6-amino-1-methyl-2,4-dioxo-3-ethyl(1,3-dihydropyrimidin-5-yl))(1-{[3-fluorophenyl]methyl}-pyrazol-4-yl)carboxamide;
N-(6-amino-1-methyl-2,4-dioxo-3-cyclopropylmethyl (1,3-dihydropyrimidin-5-yl))(1-{[3-fluorophenyl]methyl}-pyrazol-4-yl)carboxamide;
N-(6-amino-1-ethyl-2,4-dioxo-3-cyclopropylmethyl (1,3-dihydropyrimidin-5-yl))(1-{[3-fluorophenyl]methyl}-pyrazol-4-yl)carboxamide;
N-[6-amino-3-(cyclopropylmethyl)-1-methyl-2,4-dioxo(1,3-dihydropyrimidin-5-yl)][1-benzylpyrazol-4-yl]carboxamide;
N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;
[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;
N-[6-amino-3-(cyclopropylmethyl)-1-ethyl-2,4-dioxo(1,3-dihydropyrimidin-5-yl)](1-{[6-(trifluoromethyl)(3-pyridyl)]methyl}pyrazol-4-yl)carboxamide;
N-[6-amino-3-propyl)-1-ethyl-2,4-dioxo(1,3-dihydropyrimidin-5-yl)](1-{(2-pyridyl)]methyl}pyrazol-4-yl)carboxamide;
N-[6-amino-3-(2-methylpropyl)-1-methyl-2,4-dioxo(1,3-dihydropyrimidin-5-yl)][1-benzylpyrazol-4-yl]carboxamide;
N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and
N-[6-amino-3-(2-methylpropyl)-1-ethyl-2,4-dioxo(1,3-dihydropyrimidin-5-yl)](1-{[6-(trifluoromethyl)(3-pyridyl)]methyl}pyrazol-4-yl)carboxamide.

C. Preparation of a Compound of Formula (2) varying $R^1$ and $R^2$

Similarly, following the procedure of Example 7A, but optionally replacing 5,6-diamino-1-ethyl-3-propyl-1,3-dihydropyrimidine-2,4-dione with other compounds of formula (2), and optionally replacing 1-{[3-(trifluoromethyl)phenyl]methyl}pyrazole-4-carboxylic acid with other compounds of formula Z—Y—X—CO₂H, other compounds of formula (3) are prepared.

EXAMPLE 8

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

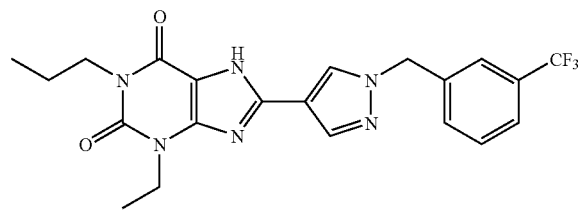 [SMILES: CCCn1c(=O)c2[nH]c(-c3cnn(Cc4cccc(C(F)(F)F)c4)c3)nc2n(CC)c1=O]

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (80 mg, 0.17 mmol), 10% aqueous sodium hydroxide (5 ml), and methanol (5 ml) was stirred at 100° C. for 2 hours. The mixture was cooled, methanol removed under reduced pressure, and the residue diluted with water and acidified with hydrochloric acid. The precipitate was filtered off, washed with water, then methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J=7.42 Hz); MS m/z 447.2 (M$^+$).

B. Preparation of a Compound of Formula I, varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl)) (1-{[3-(trifluoromethyl)phenyl]methyl}pyrazol-3-yl)carboxamide with other compounds of formula (3), the following compounds of Formula I were prepared:

1-cyclopropylmethyl-3-methyl-8-[1-(phenylmethyl)pyrazol-4-yl]-1,3,7-trihydropurine-2,6-dione;
1-cyclopropylmethyl-3-methyl-8-{1-[(3-trifluoromethylphenyl)methyl]pyrazol-4-yl}-1,3,7-trihydropurine-2,6-dione;
1-cyclopropylmethyl-3-ethyl-8-{1-[(3-trifluoromethylphenyl)methyl]pyrazol-4-yl}-1,3,7-trihydropurine-2,6-dione;
1-cyclopropylmethyl-3-methyl-8-{1-[(3-fluorophenyl)methyl]pyrazol-4-yl}-1,3,7-trihydropurine-2,6-dione;
1-cyclopropylmethyl-3-ethyl-8-{1-[(3-fluorophenyl)methyl]pyrazol-4-yl}-1,3,7-trihydropurine-2,6-dione;
1-cyclopropylmethyl-3-ethyl-8-(1-{[6-(trifluoromethyl)(3-pyridyl)]methyl}pyrazol-4-yl)-1,3,7-trihydropurine-2,6-dione;
3-({4-[1-(cyclopropylmethyl)-3-methyl-2,6-dioxo-1,3,7-trihydropurin-8-yl]pyrazolyl}methyl)benzenecarbonitrile;
8-[1-(2-(1H-1,2,3,4-tetraazol-5-yl)ethyl)pyrazol-4-yl]-3-methyl-1-cyclopropylmethyl-1,3,7-trihydropurine-2,6-dione;
1-(2-methylpropyl)-3-methyl-8-[1-benzylpyrazol-4-yl]-1,3,7-trihydropurine-2,6-dione;
1-(2-methylpropyl)-3-ethyl-8-{1-[(3-fluorophenyl)methyl]pyrazol-4-yl}-1,3,7-trihydropurine-2,6-dione;
1-(2-methylpropyl)-3-methyl-8-{1-[(3-trifluoromethylphenyl)methyl]pyrazol-4-yl}-1,3,7-trihydropurine-2,6-dione;
1-(2-methylpropyl)-3-methyl-8-{1-[(3-fluorophenyl)methyl]pyrazol-4-yl}-1,3,7-trihydropurine-2,6-dione;
3-ethyl-1-(2-methylpropyl)-8-(1-{[6-(trifluoromethyl)(3-pyridyl)]methyl}pyrazol-4-yl)-1,3,7-trihydropurine-2,6-dione;
1-ethyl-3-methyl-8-{1-[(3-fluorophenyl)methyl]pyrazol-4-yl}-1,3,7-trihydropurine-2,6-dione; and
3-ethyl-1-propyl-8-[1-(2-pyridylmethyl)pyrazol-4-yl]-1,3,7-trihydropurine-2,6-dione.

C. Preparation of a Compound of Formula I, varying $R^1$, $R^2$, X, Y, and Z

Similarly, following the procedure of Example 8A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (3), other compounds of Formula I are prepared.

EXAMPLE 9

Preparation of a Compound of Formula (10)

A. Preparation of a Compound of Formula (10) in which $R^1$ is n-Propyl

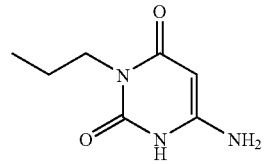

A mixture of 6-aminouracil (5.08 g, 40 mmol), hexamethyldisilazane (50 ml), and ammonium sulfate (260 mg, 1.96 mmol) was refluxed for 12 hours. After cooling, the solid was filtered off, and solvent was removed from the filtrate under reduced pressure to provide the trimethylsilylated derivative of 6-aminouracil.

The product was dissolved in toluene (1.5 ml), and iodopropane (7.8 ml, 80 mmol) and heated in an oil bath at 120° C. for 2 hours. The reaction mixture was then cooled to 0° C., and saturated aqueous sodium bicarbonate added slowly. The resulting precipitate was filtered off, and washed sequentially with water, toluene, and ether, to provide 6-amino-3-propyl-1,3-dihydropyrimidine-2,4-dione, a compound of formula (10), which was used in the next reaction with no further purification.

$^1$H-NMR (DMSO-d6) δ 10.34 (s, 1H), 6.16 (s, 2H), 4.54 (s, 1H), 3.57-3.62 (m, 2H), 1.41-1.51 (m, 2H), 0.80 (t, 3H, J=7.43 Hz).

B. Preparation of a Compound of Formula (10), varying $R^1$

Similarly, following the procedure of Example 9A, but replacing iodopropane with other alkyl halides of formula $R^1$Hal, other compounds of formula (10) are prepared, including:

6-amino-3-cyclopropylmethyl-1,3-dihydropyrimidine-2,4-dione; and 6-amino-3-(2-methylpropyl)-1,3-dihydropyrimidine-2,4-dione.

EXAMPLE 10

Preparation of a Compound of Formula (11)

A. Preparation of a Compound of Formula (10) in which $R^1$ is n-Propyl

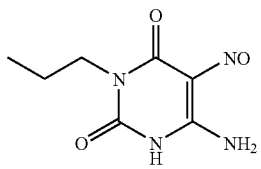

To a solution of 6-amino-3-propyl-1,3-dihydropyrimidine-2,4-dione (5.6 g) in a mixture of 50% acetic acid/water (160 ml) at 70° C. was added sodium nitrite (4.5 g) in portions over a period of 15 minutes. The mixture was stirred at 70° C. for 45 minutes, then the reaction mixture concentrated to a low volume under reduced pressure. The solid was filtered off, and washed with water, to provide 6-amino-5-nitroso-3-propyl-1,3-dihydropyrimidine-2,4-dione, a compound of formula (11).

$^1$H-NMR (DMSO-d6) δ 11.42 (s, 1H), 7.98 (s, 3.77-3.81 (m, 2H), 3.33 (s, 1H), 1.55-1.64 (m, 2H), 0.89 (t, 3H, J=7.43 Hz); MS m/z 198.78 (M$^+$), 220.78 (M$^+$+Na)

B. Preparation of a Compound of Formula (11), varying $R^1$

Similarly, following the procedure of Example 10A, but replacing 6-amino-3-propyl-1,3-dihydropyrimidine-2,4-dione with other compounds of formula (10), other compounds of formula (11) are prepared, including:

6-amino-5-nitroso-3-cyclopropylmethyl-1,3-dihydropyrimidine-2,4-dione; and
6-amino-5-nitroso-3-(2-methylpropyl)-1,3-dihydropyrimidine-2,4-dione.

EXAMPLE 11

Preparation of a Compound of Formula (12)

A. Preparation of a Compound of Formula (12) in which $R^1$ is n-Propyl

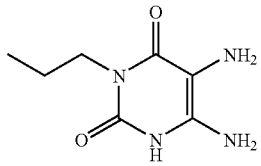

To a solution of 6-amino-5-nitroso-3-propyl-1,3-dihydropyrimidine-2,4-dione (5.4 g, 27 mmol) in 12.5% aqueous ammonia (135 ml) at 70° C. was added sodium dithionite (Na$_2$S$_2$O$_4$, 9.45 g, 54 mmol) in portions over 15 minutes, and the mixture was stirred for 20 minutes. The solution was concentrated under reduced pressure, cooled to 5° C., the precipitate filtered off, and washed with cold water, to provide 5,6-diamino-3-propyl-1,3-dihydropyrimidine-2,4-dione, a compound of formula (12).

$^1$H-NMR (DMSO-d6) δ 0.81 (t, 3H, J=7.43 Hz), 1.43-1.52 (m, 2H), 3.63-3.67 (m, 2H), 5.56 (s, 2H); MS m/z 184.95 (M$^+$), 206.96 (M$^+$+Na)

B. Preparation of a Compound of Formula (12), varying

Similarly, following the procedure of Example 11A, but replacing 6-amino-3-propyl-1,3-dihydropyrimidine-2,4-dione with other compounds of formula (11), other compounds of formula (12) are prepared, including:

5,6-diamino-3-cyclopropylmethyl-1,3-dihydropyrimidine-2,4-dione; and
5,6-diamino-3-(2-methylpropyl)-1,3-dihydropyrimidine-2,4-dione.

EXAMPLE 12

Preparation of a Compound of Formula (13)

A. Preparation of a Compound of Formula (13) in which $R^1$ is n-Propyl, X is 1,4-Pyrazolyl, Y is Methylene, and Z is 3-Trifluoromethylphenyl

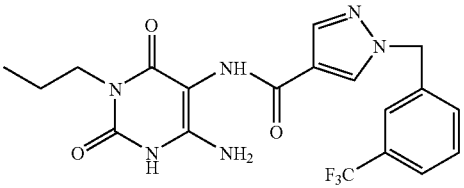 [SMILES: CCCn1c(=O)[nH]c(N)c(NC(=O)c2cnn(Cc3cccc(C(F)(F)F)c3)c2)c1=O]

To a mixture of 5,6-diamino-3-propyl-1,3-dihydropyrimidine-2,4-dione (2.3 g, 126 mmol) and 1-{[3-(trifluoromethyl)phenyl]methyl}pyrazole-4-carboxylic acid (3.79 g, 14 mmol) in methanol (50 ml) was added 1-(3-dimethylaminopropyl)-3-ethylcarbodiimide hydrochloride (2.67 g, 14 mmol), and the reaction mixture was stirred for 3 days at room temperature (although less time is acceptable). The precipitate was filtered off, and was washed sequentially with water, and methanol. The product was dried under vacuum to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

$^1$H-NMR (DMSO-d6) δ 10.44 (s, 1H), 8.56 (s, 1H), 8.37 (s, 1H), 8.00 (s, 1H), 7.56-7.71 (m, 3H), 6.02 (s, 1H), 5.49 (s, 2H), 3.62-3.66 (m, 2H), 1.44-1.53 (m, 2H), 0.82 (t, 3H, J=7.43 Hz); MS m/z 458.92 (M$^+$+Na).

B. Alternative Preparation of a Compound of Formula (3) in which $R^1$ is n-Propyl, X is 1,4-Pyrazolyl, Y is Methylene, and Z is 3-Trifluoromethylphenyl A solution of 1-{[3-(trifluoromethyl)phenyl]methyl}pyrazole-4-carboxylic acid (1 g, 3.7 mmol) in thionyl chloride (1 ml) was heated at 70° C. for 4 hours. Excess thionyl chloride was distilled off, and the residue treated with methylene chloride/hexanes. The solvent was removed under reduced pressure, and the residue dissolved in acetonitrile. This solution was added to a suspension of 5,6-diamino-3-propyl-1,3-dihydropyrimidine-2,4-dione (2.3 g, 126 mmol) and triethylamine (1 ml) in acetonitrile (20 ml) at 0° C., and stirred for 16 hours. The reaction mixture was quenched with water (5 ml), acidified with hydrochloric acid, stirred for 30 minutes, and the precipitate filtered off. The product was washed with ether, to provide N-(6-amino-2,4-dioxo-3-propyl(1,3-dihydropyrimidin-5-yl))(1-{[3-(trifluoromethyl)phenyl]methyl}pyrazol-4-yl)carboxamide, a compound of formula (13).

C. Preparation of a Compound of Formula (13), varying R¹, X, Y, and Z

Similarly, following the procedure of Example 12A or 12B, but optionally replacing 6-amino-3-propyl-1,3-dihydropyrimidine-2,4-dione with other compounds of formula (12), and optionally replacing 1-{[3-(trifluoromethyl)phenyl]methyl}pyrazole-4-carboxylic acid with other compounds of formula Z—Y—X—CO₂H, other compounds of formula (13) are prepared, including:

N-(6-amino-2,4-dioxo-3-cyclopropylmethyl (1,3-dihydropyrimidin-5-yl))(1-{[3-(trifluoromethyl)phenyl]methyl}pyrazol-4-yl)carboxamide;

N-(6-amino-2,4-dioxo-3-(2-methylpropyl)(1,3-dihydropyrimidin-5-yl))(1-{[3-(trifluoromethyl)phenyl]methyl}pyrazol-4-yl)carboxamide;

N-(6-amino-2,4-dioxo-3-propyl(1,3-dihydropyrimidin-5-yl))(1-{[3-fluorophenyl]methyl}pyrazol-4-yl)carboxamide;

N-(6-amino-2,4-dioxo-3-cyclopropylmethyl(1,3-dihydropyrimidin-5-yl))(1-{[3-fluorophenyl]methyl}pyrazol-4-yl)carboxamide;

N-(6-amino-2,4-dioxo-3-(2-methylpropyl)(1,3-dihydropyrimidin-5-yl))(1-{[3-fluorophenyl]methyl}pyrazol-4-yl)carboxamide;

N-(6-amino-2,4-dioxo-3-propyl(1,3-dihydropyrimidin-5-yl))(1-[1-benzyl]pyrazol-4-yl)carboxamide;

N-(6-amino-2,4-dioxo-3-cyclopropylmethyl (1,3-dihydropyrimidin-5-yl))(1-[1-benzyl]pyrazol-4-yl)carboxamide;

N-(6-amino-2,4-dioxo-3-(2-methylpropyl)(1,3-dihydropyrimidin-5-yl))(1-[1-benzyl]pyrazol-4-yl)carboxamide;

N-(6-amino-2,4-dioxo-3-propyl(1,3-dihydropyrimidin-5-yl))(1-{[3-cyanophenyl]methyl}pyrazol-4-yl)carboxamide;

N-(6-amino-2,4-dioxo-3-cyclopropylmethyl(1,3-dihydropyrimidin-5-yl))(1-{[3-cyanophenyl]methyl}pyrazol-4-yl)carboxamide;

N-(6-amino-2,4-dioxo-3-(2-methylpropyl)(1,3-dihydropyrimidin-5-yl))(1-{[3-cyanophenyl]methyl}pyrazol-4-yl)carboxamide;

N-(6-amino-2,4-dioxo-3-propyl(1,3-dihydropyrimidin-5-yl))(1-{[1-(2-(1H-1,2,3,4-tetraazol-5-yl)ethyl)pyrazol-4-yl}carboxamide;

N-(6-amino-2,4-dioxo-3-cyclopropylmethyl(1,3-dihydropyrimidin-5-yl))(1-{[1-(2-(1H-1,2,3,4-tetraazol-5-yl)ethyl)pyrazol-4-yl)carboxamide;

N-(6-amino-2,4-dioxo-3-(2-methylpropyl)(1,3-dihydropyrimidin-5-yl))(1-{[1-(2-(1H-1,2,3,4-tetraazol-5-yl)ethyl)pyrazol-4-yl)carboxamide;

N-(6-amino-2,4-dioxo-3-propyl(1,3-dihydropyrimidin-5-yl))(1-{[6-(trifluoromethyl)(3-pyridyl)]methyl}pyrazol-4-yl)carboxamide;

N-(6-amino-2,4-dioxo-3-cyclopropylmethyl(1,3-dihydropyrimidin-5-yl))(1-{[6-(trifluoromethyl)(3-pyridyl)]methyl}pyrazol-4-yl)carboxamide; and N-(6-amino-2,4-dioxo-3-(2-methylpropyl)(1,3-dihydropyrimidin-5-yl))(1-{[6-(trifluoromethyl)(3-pyridyl)]methyl}pyrazol-4-yl)carboxamide.

EXAMPLE 13

Preparation of a Compound of Formula (3)

A. Preparation of a Compound of Formula (3) in which R¹ is n-Propyl, R² is Ethyl, X is 1,4-Pyrazolyl, Y is Methylene, and Z is 3-Trifluoromethylphenyl

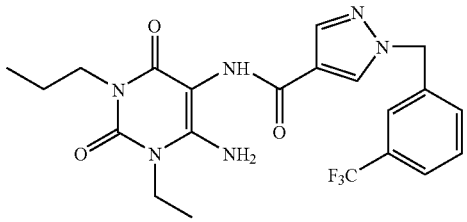 [SMILES: CCCn1c(=O)c(NC(=O)c2cnn(Cc3cccc(C(F)(F)F)c3)c2)c(N)n(CC)c1=O]

A mixture of a solution of N-(6-amino-2,4-dioxo-3-propyl(1,3-dihydropyrimidin-5-yl))(1-{[3-(trifluoromethyl)-phenyl]methyl}pyrazol-3-yl)carboxamide (872 mg, 2 mmol) in dimethylformamide (10 ml), potassium carbonate (552 mg, 4 mmol) and ethyl iodide (0.24 ml, 3 mmol) was stirred at room temperature overnight. The reaction mixture was filtered, and the solvent was evaporated from the filtrate under reduced pressure. The residue was stirred with water for two hours at room temperature, and the precipitate filtered off, washed with water, and then dissolved in methanol. The solvent was then removed under reduced pressure to provide N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide, a compound of formula (3).

¹H-NMR. (DMSO-d6): δ 8.58 (s, 1H), 8.39 (s, 1H), 8.01 (s, 1H), 7.72-7.50 (m, 4H), 6.71 (s, 2H), 5.51 (s, 2H), 4.0-3.82 (m, 2H), 3.77-3.65 (m, 2H), 1.60-1.50 (m, 2H), 1.13 (t, 3H, J=6.8 Hz), 0.84 (t, 3H, J=7.2 Hz); MS m/z 462.9 (M⁻)

B. Preparation of a Compound of Formula (13), varying R¹, X, Y, and Z

Similarly, following the procedure of Example 13A, but replacing N-(6-amino-2,4-dioxo-3-propyl(1,3-dihydropyrimidin-5-yl))(1-{[3-(trifluoromethyl)-phenyl]methyl}pyrazol-3-yl)carboxamide with other compounds of formula (13), other compounds of formula (3) are prepared, including:

N-(6-amino-1-methyl-2,4-dioxo-3-propyl(1,3-dihydropyrimidin-5-yl))(1-{[3-(trifluoromethyl)phenyl]methyl}-pyrazol-4-yl)carboxamide;

N-(6-amino-1-methyl-2,4-dioxo-3-cyclopropylmethyl(1,3-dihydropyrimidin-5-yl))(1-{[3-(trifluoromethyl)phenyl]methyl}-pyrazol-4-yl)carboxamide;

N-(6-amino-1-ethyl-2,4-dioxo-3-cyclopropylmethyl (1,3-dihydropyrimidin-5-yl))(1-{[3-(trifluoromethyl)phenyl]methyl}-pyrazol-4-yl)carboxamide;

N-(6-amino-1-methyl-2,4-dioxo-3-ethyl(1,3-dihydropyrimidin-5-yl))(1-{[3-fluorophenyl]methyl}-pyrazol-4-yl)carboxamide;

N-(6-amino-1-methyl-2,4-dioxo-3-cyclopropylmethyl(1,3-dihydropyrimidin-5-yl))(1-{[3-fluorophenyl]methyl}-pyrazol-4-yl)carboxamide;

N-(6-amino-1-ethyl-2,4-dioxo-3-cyclopropylmethyl (1,3-dihydropyrimidin-5-yl))(1-{[3-fluorophenyl]methyl}-pyrazol-4-yl)carboxamide;

N-[6-amino-3-(cyclopropylmethyl)-1-methyl-2,4-dioxo(1,3-dihydropyrimidin-5-yl)][1-benzylpyrazol-4-yl]carboxamide;

N-(6-amino-1-methyl-2,4-dioxo-3-cyclopropylmethyl(1,3-dihydropyrimidin-5-yl))(1-{[3-cyanophenyl]methyl}-pyrazol-4-yl)carboxamide;
[1-(2-(1H-1,2,3,4-tetraazol-5-yl)ethyl)pyrazol-4-yl]-N-[6-amino-3-(cyclopropylmethyl)-1-methyl-2,4-dioxo(1,3-dihydropyrimidin-5-yl)]carboxamide;
N-[6-amino-3-(cyclopropylmethyl)-1-ethyl-2,4-dioxo(1,3-dihydropyrimidin-5-yl)](1-{[6-(trifluoromethyl)(3-pyridyl)]methyl}pyrazol-4-yl)carboxamide;
N-[6-amino-3-propyl)-1-ethyl-2,4-dioxo(1,3-dihydropyrimidin-5-yl)](1-{(2-pyridyl)]methyl}pyrazol-4-yl)carboxamide;
N-[6-amino-3-(2-methylpropyl)-1-methyl-2,4-dioxo(1,3-dihydropyrimidin-5-yl)][1-benzylpyrazol-4-yl]carboxamide;
N-[6-amino-3-(2-methylpropyl)-1-methyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-ethyl-2,4-dioxo(1,3-dihydropyrimidin-5-yl)][1-{[3-fluorophenyl]methyl}pyrazol-4-yl]carboxamide;
N-[6-amino-3-(2-methylpropyl)-1-methyl-2,4-dioxo(1,3-dihydropyrimidin-5-yl)][1-{[3-(trifluoromethyl)phenyl]methyl}pyrazol-4-yl]carboxamide; and
N-[6-amino-3-(2-methylpropyl)-1-ethyl-2,4-dioxo(1,3-dihydropyrimidin-5-yl)](1-{[6-(trifluoromethyl)(3-pyridyl)]methyl}pyrazol-4-yl)carboxamide.

EXAMPLE 14

Preparation of a Compound of Formula I

A. Preparation of a Compound of Formula I in which $R^1$ is n-Propyl, $R^2$ is Ethyl, X is 1,4-Pyrazolyl, Y is Methylene, and Z is 3-Trifluoromethylphenyl

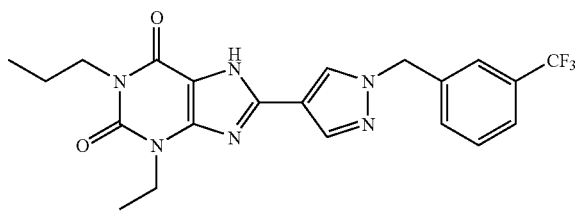 [SMILES: CCCn1c(=O)c2[nH]c(-c3cnn(Cc4cccc(C(F)(F)F)c4)c3)nc2n(CC)c1=O]

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (850 mg, 2.34 mmol), 10% aqueous sodium hydroxide (10 ml), and methanol (10 ml) was stirred at 100° C. for 18 hours. The mixture was cooled, methanol removed under reduced pressure, and the remaining mixture was acidified with hydrochloric acid to pH 2. The precipitate was filtered off, washed with water/methanol mixture, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J=7.42 Hz); MS m/z 447.2 (M$^+$)

B. Preparation of a Compound of Formula I, varying $R^1$, $R^2$, X, Y, and Z

Similarly, following the procedure of Example 14A, but replacing N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide with other compounds of formula (13), other compounds of Formula I are prepared, including those listed in Example 8.

EXAMPLE 15

Preparation of a Compound of Formula (14)

A. Preparation of a Compound of Formula (14) in which $R^2$ is Ethyl

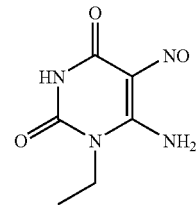

To a solution of 6-amino-1-ethyl-1,3-dihydropyrimidine-2,4-dione (5.0 g, 32.3 mmol) in a mixture of 50% acetic acid/water (50 ml) at 70° C. was added sodium nitrite (4.45 g, 64.5 mmol) in portions over a period of 30 minutes. The mixture was stirred at 70° C. for a further 30 minutes. The reaction mixture was cooled, and the precipitate filtered off, and washed with water, then methanol, to provide 6-amino-1-ethyl-5-nitroso-1,3-dihydropyrimidine-2,4-dione, a compound of formula (14).

$^1$H-NMR (DMSO-d6): δ 11.52 (s, 1H), 9.16 (s, 1H), 3.83 (q, 2H, J=7.0 Hz), 1.11 (t, 3H, 7.0 Hz). MS m/z 184.8 (M$^+$), 206.80 (M$^+$+Na)

B. Preparation of a Compound of Formula (14), varying $R^2$

Similarly, following the procedure of Example 15A, but replacing 6-amino-1-ethyl-1,3-dihydropyrimidine-2,4-dione with 6-amino-1-methyl-1,3-dihydropyrimidine-2,4-dione, 6-amino-1-methyl-5-nitroso-1,3-dihydropyrimidine-2,4-dione was prepared.

C. Preparation of a Compound of Formula (14), varying $R^2$

Similarly, following the procedure of Example 15A, but replacing 6-amino-1-ethyl-1,3-dihydropyrimidine-2,4-dione with other compounds of formula (5), other compounds of formula (14) are prepared.

EXAMPLE 16

Preparation of a Compound of Formula (15)

A. Preparation of a Compound of Formula (15) in which $R^2$ is Ethyl

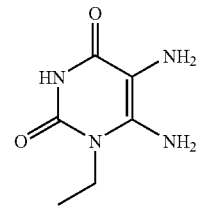

To a solution of 6-amino-1-ethyl-5-nitroso-1,3-dihydropyrimidine-2,4-dione (3.9 g, 21.2 mmol) in 14.5% aqueous ammonia (50 ml) at 50° C. was added sodium dithionite (Na$_2$S$_2$O$_4$, 7.37 g, 42.4 mmol) in portions over 15 minutes, and the mixture was stirred for 20 minutes. The solution was concentrated under reduced pressure to a volume of 30 ml, cooled to 5° C., the precipitate filtered off, and washed with cold water, to provide 5,6-diamino-1-ethyl-1,3-dihydropyrimidine-2,4-dione, a compound of formula (15).

$^1$H-NMR (DMSO-d6): δ 10.58 (s, 1H), 6.18 (s, 2H), 3.83 (q, 2H, J=7.2 Hz), 2.82 (s, 2H), 1.10 (t, 3H, J=7.2 Hz).

B. Preparation of a Compound of Formula (15), varying $R^2$

Similarly, following the procedure of Example 16A, but replacing 6-amino-1-ethyl-5-nitroso-1,3-dihydropyrimidine-2,4-dione with 6-amino-1-methyl-5-nitroso-1,3-dihydropyrimidine-2,4-dione, 5,6-diamino-1-methyl-1,3-dihydropyrimidine-2,4-dione was prepared.

C. Preparation of a Compound of Formula (15), varying $R^2$

Similarly, following the procedure of Example 16A, but replacing 6-amino-1-ethyl-5-nitroso-1,3-dihydropyrimidine-2,4-dione with other compounds of formula (14), other compounds of formula (15) are prepared.

EXAMPLE 17

Preparation of a Compound of Formula (16)

A. Preparation of a Compound of Formula (16) in which $R^2$ is Ethyl, X is 1,4-Pyrazolyl, Y is Methylene, and Z is 3-Trifluoromethylphenyl

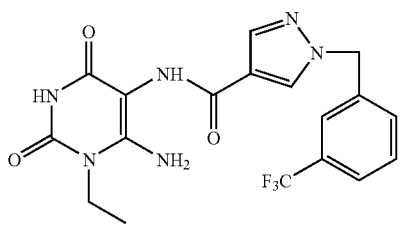 [SMILES: CCn1c(N)c(NC(=O)c2cnn(Cc3cccc(C(F)(F)F)c3)c2)c(=O)[nH]c1=O]

To a mixture of 5,6-diamino-1-ethyl-1,3-dihydropyrimidine-2,4-dione (2 g, 11.76 mmol) and 1-{[3-(trifluoromethyl)phenyl]methyl}pyrazole-4-carboxylic acid (3.5 g, 12.94 mmol) in methanol (50 ml) was added 1-(3-dimethylaminopropyl)-3-ethylcarbodiimide hydrochloride (2.47 g, 12.94 mmol), and the reaction mixture was stirred for 16 hours at room temperature. Solvent was removed under reduced pressure, and the residue was washed with water and methanol. The product was dried under vacuum to provide N-(6-amino-1-ethyl-2,4-dioxo(1,3-dihydropyrimidin-5-yl))(1-{[3-(trifluoromethyl)phenyl]methyl}pyrazol-4-yl)carboxamide, a compound of formula (16).

$^1$H-NMR (DMSO-d6): δ 10.60 (s, 1H), 8.50 (s, 1H), 8.39 (s, 1H), 8.01 (s, 1H), 7.72-7.50 (m, 4H), 6.69 (s, 2H), 5.50 (s, 2H), 3.87 (q, 2H, J=7.2 Hz), 1.11 (t, 3H, 7.2 Hz); MS m/z 421 (M$^-$)

B. Preparation of a Compound of Formula (16), varying $R^2$, X, Y, and Z

Similarly, following the procedure of Example 17A, but replacing 5,6-diamino-1-ethyl-1,3-dihydropyrimidine-2,4-dione with 5,6-diamino-1-methyl-1,3-dihydropyrimidine-2,4-dione, N-(6-amino-1-methyl-2,4-dioxo(1,3-dihydropyrimidin-5-yl))(1-{[3-(trifluoromethyl)phenyl]methyl}pyrazol-4-yl)carboxamide was prepared.

C. Preparation of a Compound of Formula (16), varying $R^2$, X, Y, and Z

Similarly, following the procedure of Example 16A, but replacing 5,6-diamino-1-ethyl-1,3-dihydropyrimidine-2,4-dione with other compounds of formula (14), other compounds of formula (15) are prepared.

EXAMPLE 18

Preparation of a Compound of Formula (3)

A. Preparation of a Compound of Formula (3) in which $R^1$ is n-Propyl, $R^2$ is Ethyl, X is 1,4-Pyrazolyl, Y is Methylene, and Z is 3-Trifluoromethylphenyl

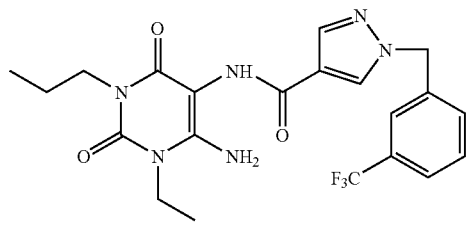 [SMILES: CCCn1c(=O)c(NC(=O)c2cnn(Cc3cccc(C(F)(F)F)c3)c2)c(N)n(CC)c1=O]

A mixture of a solution of N-(6-amino-1-ethyl-2,4-dioxo (1,3-dihydropyrimidin-5-yl))(1-{[3-(trifluoromethyl)phenyl]methyl}pyrazol-3-yl)carboxamide (1.5 g, 3.55 mmol) in dimethylformamide (30 ml), potassium carbonate (980 mg, 7.1 mmol) and propyl iodide (724 mg, 4.26 mmol) was stirred at room temperature overnight. Water was added, and the precipitate filtered off, to provide N-(6-amino-1-ethyl-2,4-dioxo-3-propyl(1,3-dihydropyrimidin-5-yl))(1-{[3-(trifluoromethyl)phenyl]methyl}pyrazol-4-yl)carboxamide, a compound of formula (3), which was used in the next reaction with no further purification.

$^1$H-NMR (DMSO-d6): δ 8.58 (s, 1H), 8.39 (s, 1H), 8.01 (s, 1H), 7.72-7.50 (m, 4H), 6.71 (s, 2H), 5.51 (s, 2H), 4.0-3.82 (m, 2H), 3.77-3.65 (m, 2H), 1.60-1.50 (m, 2H), 1.13 (t, 3H, J=6.8 Hz), 0.84 (t, 3H, J=7.2 Hz); MS m/z 462.9 (M$^-$)

B. Preparation of a Compound of Formula (3), varying $R^1$, $R^2$, X, Y, and Z

Similarly, following the procedure of Example 18A, but replacing N-(6-amino-1-ethyl-2,4-dioxo(1,3-dihydropyrimidin-5-yl))(1-{[3-(trifluoromethyl)phenyl]-methyl}pyrazol-3-yl)carboxamide with N-(6-amino-1-methyl-2,4-dioxo(1,3-dihydropyrimidin-5-yl)), N-(6-amino-1-methyl-2,4-dioxo-3-propyl(1,3-dihydropyrimidin-5-yl))(1-{[3-(trifluoromethyl)phenyl]methyl}pyrazol-4-yl)carboxamide was prepared.

C. Preparation of a Compound of Formula (3), varying $R^1$, $R^2$, X, Y, and Z

Similarly, following the procedure of Example 18A, but optionally replacing N-(6-amino-1-ethyl-2,4-dioxo(1,3-dihydropyrimidin-5-yl))(1-{[3-(trifluoromethyl)phenyl] methyl}pyrazol-3-yl)carboxamide with other compounds of formula (15), and optionally replacing propyl iodide with other compounds of formula $R^1$Hal, other compounds of formula (3) are prepared.

EXAMPLE 19

Preparation of a Compound of Formula

A. Preparation of a Compound of Formula 1 in which $R^1$ is n-Propyl, $R^2$ is Ethyl, X is 1,4-Pyrazolyl, Y is Methylene, and Z is 3-Trifluoromethylphenyl

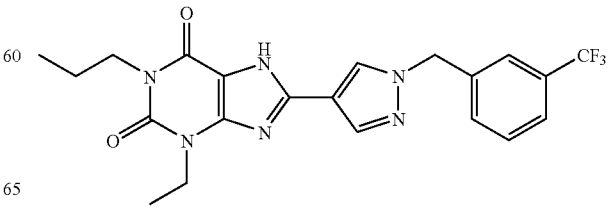

A mixture of N-(6-amino-1-ethyl-2,4-dioxo-3-propyl(1,3-dihydropyrimidin-5-yl))(1-{[3-(trifluoromethyl)phenyl]methyl}pyrazol-3-yl)carboxamide (300 mg, 464 mmol), 20% aqueous sodium hydroxide (5 ml), and methanol (10 ml) was stirred at 80° C. for 3 hours. The mixture was cooled, methanol removed under reduced pressure, and the remaining mixture was acidified with hydrochloric acid to pH 2. The precipitate was filtered off, washed with water and methanol, to provide 3-ethyl-1-propyl-8-(1-{[3-(trifluoromethyl)phenyl]methyl}pyrazol-4-yl)-1,3,7-trihydropurine-2,6-dione, a compound of Formula I.

$^1$H-NMR (DMSO-d6) δ 8.57 (s, 1H), 8.15 (s, 1H), 7.60-7.75 (m, 4H), 5.54 (s, 2H), 4.05-4.50 (m, 2H), 3.87-3.91 (m, 2H), 1.55-1.64 (m, 2H), 1.25 (t, 3H, J=7.03 Hz), 0.90 (t, 3H, J=7.42 Hz); MS m/z 447.2 ($M^+$)

EXAMPLE 20

Characterization of $A_{2B}$ Antagonists

Radioligand Binding for $A_{2B}$ Adenosine Receptor

Human $A_{2B}$ adenosine receptor cDNA was stably transfected into HEK-293 cells (referred to as HEK-A2B cells). Monolayers of HEK-A2B cells were washed with PBS once and harvested in a buffer containing 10 mM HEPES (pH 7.4), 10 mM EDTA and protease inhibitors. These cells were homogenized in polytron for 1 minute at setting 4 and centrifuged at 29000 g for 15 minutes at 4° C. The cell pellets were washed once with a buffer containing 10 mM HEPES (pH7.4), 1 mM EDTA and protease inhibitors, and were resuspended in the same buffer supplemented with 10% sucrose. Frozen aliquots were kept at −80° C.

Competition assays were started by mixing 10 nM $^3$H-ZM241385 (Tocris Cookson) with various concentrations of test compounds and 50 μg membrane proteins in TE buffer (50 mM Tris and 1 mM EDTA) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 10 μM ZM241385. The affinities of compounds (I.e. Ki values) were calculated using GraphPad software.

Radioligand Binding for Other Adenosine Receptors

Human $A_1$, $A_{2A}$, $A_3$ adenosine receptor cDNAs were stably transfected into either CHO or HEK-293 cells (referred to as CHO-$A_1$, HEK-$A_{2A}$, CHO-$A_3$). Membranes were prepared from these cells using the same protocol as described above. Competition assays were started by mixing 0.5 nM $^3$H-CPX (for CHO-$A_1$), 2 nM $^3$H-ZM214385 (HEK-$A_{2A}$) or 0.1 nM $^{125}$I-AB-MECA (CHO-$A_3$) with various concentrations of test compounds and the perspective membranes in TE buffer (50 mM Tris and 1 mM EDTA of CHO-$A_1$ and HEK-$A_{2A}$) or TEM buffer (50 mM. Tris, 1 mM EDTA and 10 mM MgCl2 for CHO-$A_3$) supplemented with 1 Unit/mL adenosine deaminase. The assays were incubated for 90 minutes, stopped by filtration using Packard Harvester and washed four times with ice-cold TM buffer (10 mM Tris, 1 mM MgCl2, pH 7.4). Non specific binding was determined in the presence of 1 μM CPX (CHO-$A_1$), 1 μM ZM241385 (HEK-$A_{2A}$) and 1 μM IB-MECA (CHO-$A_3$). The affinities of compounds (I.e. Ki values) were calculated using GraphPad™ software.

cAMP Measurements

Monolayer of transfected cells were collected in PBS containing 5 mM EDTA. Cells were washed once with DMEM and resuspended in DMEM containing 1 Unit/mL adenosine deaminase at a density of 100,000-500,000 cells/ml. 100 μl of the cell suspension was mixed with 25 μl containing various agonists and/or antagonists and the reaction was kept at 37° C. for 15 minutes. At the end of 15 minutes, 125 μl 0.2N HCl was added to stop the reaction. Cells were centrifuged for 10 minutes at 1000 rpm. 100 μl of the supernatant was removed and acetylated. The concentrations of cAMP in the supernatants were measured using the direct cAMP assay from Assay Design. $A_{2A}$ and $A_{2B}$ adenosine receptors are coupled to Gs proteins and thus agonists for $A_{2A}$ adenosine receptor (such as CGS21680) or for $A_{2A}$ adenosine receptor (such as NECA) increase the cAMP accumulations whereas the antagonists to these receptors prevent the increase in cAMP accumulations-induced by the agonists. $A_1$ and $A_3$ adenosine receptors are coupled to Gi proteins and thus agonists for $A_1$ adenosine receptor (such as CPA) or for $A_3$ adenosine receptor (such as IB-MECA) inhibit the increase in cAMP accumulations-induced by forskolin. Antagonists to $A_1$ and $A_3$ receptors prevent the inhibition in cAMP accumulations.

EXAMPLE 21

Effect of $A_{2B}$ Antagonist on Airway Restructuring in Mouse Model

The model system being used is the adenosine deaminase (ADA)-deficient mouse model of adenosine-dependent pulmonary injury. In this model, elevations in adenosine are associated with increased pulmonary inflammation and airway remodeling. Many of the features seen in these mice resemble those observed in patients with various forms of chronic lung disease including severe asthma, COPD and pulmonary fibrosis. The approach is to treat these mice with the $A_{2B}$ AR antagonist 3-ethyl-1-propyl-8-{1-[(3-trifluoromethylphenyl)methyl]pyrazol -4-yl}-1,3,7-trihydropurine-2,6-dione as a means to probe $A_{2B}$AR contributions to pulmonary inflammation and injury in ADA-deficient mice, which should provide insight into the efficacy of this drug for the treatment of chronic lung diseases.

Mice treated by intraperitoneal (ip) injection twice daily with 1 mg/kg 3-ethyl-1-propyl-8-{1-[(3-trifluoromethylphenyl)methyl]pyrazol-4-yl}1,3,7-trihydropurine-2,6-dione.

The specific protocol is as follows: ADA-deficient (ADA−/−) or ADA containing (ADA+) mice were identified at birth by screening of ADA enzymatic activity in the blood. ADA−/− mice were maintained on ADA enzyme therapy from postnatal day 2 until postnatal day 21. At this stage, treatments with 3-ethyl-1-propyl-8-{1-[(3-trifluoromethylphenyl)methyl]pyrazol -4-yl}-1,3,7-trihydropurine-2,6-dione or vehicle controls (corn oil/ethanol/DMSO) were initiated. Treatments consisted of an ip injection in the morning (8-9 AM) and in the evening (5-6 pm). Treatments were given daily for 17 days, and the experiment was terminated on postnatal day 38. Treatment groups included ADA−/− or ADA+mice receiving 3-ethyl-1-propyl-8-{1-[(3-trifluoromethylphenyl)methyl]pyrazol-4-yl}-1,3,7-trihydropurine-2,6-dione, vehicle, or no treatment. All mice were littermates and were therefore strain matched. Both males and females were included in these experiments. At the termination of the experiment, serum was collected for pharmacokinetics (PK) analysis of 3-ethyl-1-propyl -8-{1-[(3-trifluoromethylphenyl)methyl]pyrazol-4-yl}-1,3,7-trihydropurine -2,6-dione levels and various pulmonary endpoints were examined.

Results from these studies indicate that treatment of ADA−/− mice with 3-ethyl-1-propyl -8-{1-[(3-trifluoromethylphenyl)methyl]pyrazol-4-yl}-1 ,3,7-trihydropurine-2, 6-dione resulted in a significant reduction in pulmonary inflammation and airway destruction. Perhaps the most dramatic observation from this study was the general health of the animals at the end of the treatment protocol. ADA−/− mice either treated with vehicle or untreated exhibited outward signs of severe respiratory distress that included rapid breathing and hunched posture. These features were not observed in ADA−/− mice treated with 3-ethyl -1-propyl-8-{1-[(3-trifluoromethylphenyl)methyl]pyrazol-4-yl}-1,3,7-trihydropurine-2,6-dione.

Methods:

Mice

ADA-deficient mice were generated and genotyped as described (Blackburn et al. (1998) *J Biol Chem* 273:5093-5100 and Young et al. (2004) *J. Immunol.* 173:1380-1389. Mice homozygous for the null Ada allele were designated ADA-deficient (ADA$^{-/-}$), while mice heterozygous for the null Ada allele were designated as ADA control mice (ADA$^+$). All mice were on a mixed 129sv/C57BL/6J background and all phenotypic comparisons were performed amongst littermates. Animal care was in accordance with institutional and NIH guidelines. Mice were housed in ventilated cages equipped with microisolator lids and maintained under strict containment protocols. No evidence of bacterial, parasitic, or fungal infection was found, and serologies on cage littermates were negative for 12 of the most common murine viruses.

Cellular Differentials and Histology

Mice were anesthetized with avertin, and lungs were lavaged four times with 0.3 ml PBS, and 0.95-1 ml of pooled lavage fluid was recovered. Total cell counts were determined using a hemocytometer, and aliquots were cytospun onto microscope slides and stained with Diff-Quick (Dade Nehring) for cellular differentials. Lungs were then infused with 4% paraformaldehyde in PBS at 25 cm of pressure and then fixed overnight at 4° C. Fixed lung samples were rinsed in PBS, dehydrated, and embedded in paraffin. Sections (5 µm) were collected on microscope slides and stained with hematoxylin and eosin (H&E; Shandon-Lipshaw) or Masson's trichrome (EM Science), according to manufacturer's instructions.

Analysis of mRNA

Mice were anesthetized and the lungs were rapidly removed and frozen in liquid nitrogen. RNA was isolated from frozen lung tissue using TRIzol Reagent (Life Technologies Inc., Grand Island, N.Y., USA). RNA samples were then DNase treated and subjected to quantitative real-time RT-PCR. The primers, probes and procedures for real-time RT-PCR were described previously in Sun et al. (2005) *J Clin Invest* 115:35-43. Reactions were carried out on a Smart Cycler rapid thermal cycler system (Cepheid, Sunnyvale, Calif.). Specific transcript levels were determined using Smart Cycler analysis software through comparison to a standard curve generated from the PCR amplification of template dilutions.

Collagen Quantification

The Sircol collagen assay (Biocolor Ltd., Belfast N. Ireland) was performed on snap frozen whole lungs. Lungs were homogenized in 5 ml. 0.5M. Acetic acid with 20 mg of pepsin and incubated with shaking for 24 hrs at 4° C. Homogenate was spun at 4000 rpm and supernatant was assayed for pepsin soluble collagen according to manufacture's instructions.

α-SMA and TGF-β1 Immunohistochemistry

Immunohistochemistry was performed on 5 µm sections cut from formalin-fixed, paraffin embedded lungs. Sections were rehydrated through graded ethanols to water, endogenous peroxidases were quenched with 3% hydrogen peroxide, antigen retrieval was performed (DAKO Corp., Carpenteria, Calif.), and endogenous avidin and biotin was blocked with the Biotin Blocking System (DAKO Corp.). For a-smooth muscle actin (sma) staining, slides were processed with the Mouse on Mouse Kit, and the ABC Elite Streptavidin Reagents (Vector Laboratories, Burlingame, Calif.) and incubated with a 1:500 dilution of a a-sma monoclonal antibody (Sigma, monoclonal clonel A-4) overnight at 4° C. Sections were developed with DAB (Sigma) and counterstained with Methyl Green.

Determination of Alveolar Airspace Size

The size of alveolar airways was determined in pressure infused lungs by measuring mean chord lengths on H&E-stained lung sections (Blackburn et al. (2000) *J Exp Med* 192:159-170). Representative images were digitized, and a grid consisting of 53 black lines at 10.5-µm intervals was overlaid on the image. This line grid was subtracted from the lung images using Image-Pro® Plus (Media Cybernetics) image analysis software, and the resultant lines were measured and averaged to give the mean chord length of the alveolar airways. The final mean chord lengths represent averages from 10 non-overlapping images of each lung specimen. All quantitative studies were performed blinded with regards to animal genotype.

Results

Histological Analysis

Histological analysis of lungs are shown in FIG. 1. The lungs of ADA−/− mice treated with vehicle exhibited significant alveolar airway simplification (FIG. 1B) and increased pulmonary inflammation that consisted predominantly of accumulation of activated macrophages in the distal airways (FIG. 1E). However, peribronchial/perivascular inflammation was also evident (not shown). Alveolar airway simplification and pulmonary inflammation was not evident in ADA+ vehicle treated (*Figure* 1A and D) or 3-ethyl-1-propyl-8-{1-[(3-trifluoromethylphenyl)methyl]pyrazol-4-yl}-1,3,7-trihydropurine-2,6-dione or untreated mice (not shown). Treatment of ADA−/− mice with the adenosine $A_{2B}$ receptor antagonist resulted in a significant decrease in alveolar airway simplification (FIG. 1C) and pulmonary inflammation (FIG. 1F). These findings indicate that treatment with an $A_{2B}$ adenosine receptor antagonist can prevent the development of pulmonary inflammation and airway destruction in ADA−/− mice.

Bronchiolalveolar Lavage Analysis

Figure 2A:
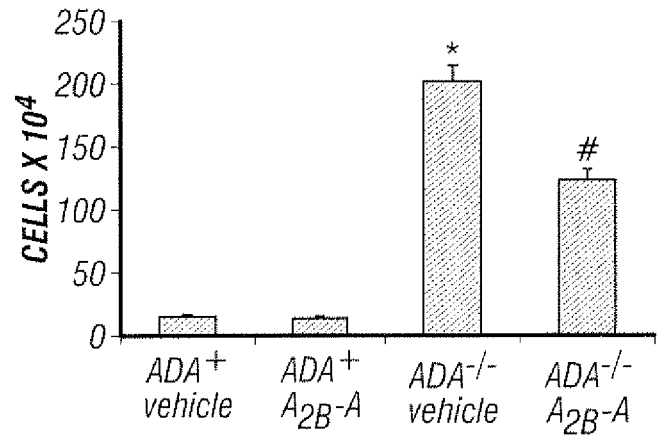
FIG. 2 shows the effects of an adenosine $A_{2B}$ receptor antagonist ($A_{2B}$-A) on airway cellularity as described in Example 21. (A) Mice were lavalged with PBS and total cell counts determined. (B and C) Cells were cytospun onto microscope slides, stained with DiffQuick and cellular differentials were determined by counting at least 200 cells per sample. Values are presented as mean total cells×$10^4$± SEM. *, significant at p<0.05 compared to ADA$^+$ animals using the students T test, n=8; #, significant at p<0.05 compared to vehicle-treated ADA$^{-/-}$ mice using the students T test, n=6-8.
Figure 2B:
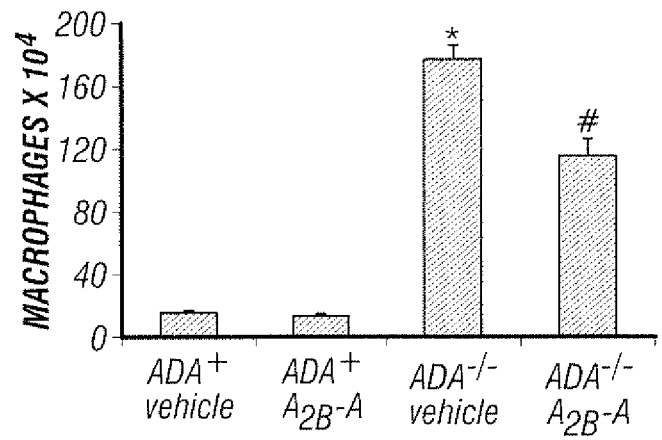

Bronchiolalveolar lavage (BAL) was performed and airway cell counts and differentials were determined (FIG. 2). Results revealed that there was a significant reduction in the number of total cells recovered from BAL of ADA−/− mice treated with the $A_{2B}$ adenosine receptor antagonist as compared to vehicle treated ADA−/− mice (FIG. 2A). Analysis of cellular differentials from BALs revealed a reduction in all cell types examined including lymphocytes, neutrophils, eosinophils (FIG. 2C) and alveolar macrophages (FIG. 2B) in ADA−/− mice treated with the $A_{2B}$ adenosine receptor antagonist.

Figure 1E:
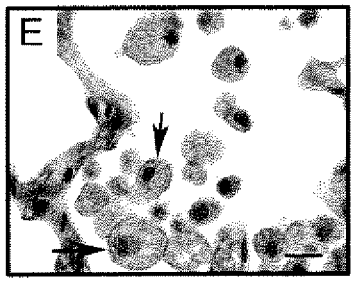
Figure 1F:

Examination of alveolar macrophages within the lungs of ADA−/− mice with and without $A_{2B}$ adenosine receptor antagonist treatment indicate that there was a difference in the degree of alveolar macrophage activation (compare FIGS. 1E and F). These observations were confirmed by quantifying the number of activated macrophages recovered from the BAL (FIG. 2C). In addition, reduction in alveolar macrophage activation can be appreciated by directly examining BAL cells cytospun onto microscope slides (FIG. 3). These data demonstrate that there is a significant decrease in airway inflammation in ADA−/− mice treated with an $A_{2B}$ adenosine receptor antagonist showing that $A_{2B}$AR antagonism can prevent airway inflammation in mammals that are genetically and/or environmentally predisposed to airway remodeling.

Effect on Inflammatory Markers

Figure 4A:
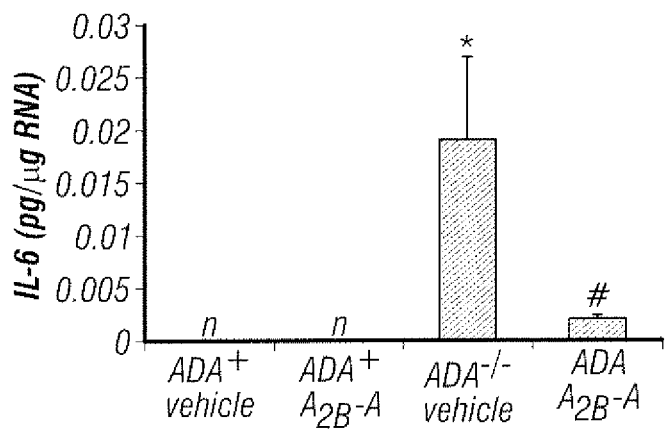
FIG. 4 illustrates transcript levels of various pro-inflammatory cytokines were measure in whole lung extracts using quantitative RT-PCR as described in Example 21. (A) IL-6 (B) Eotaxin 1 (C) TARC. Results are presented as mean pg transcripts±SEM. *, significant at p<0.05 compared to ADA$^+$ animals using the students T test; #, significant at p<0.05 compared to vehicle-treated ADA$^{-/-}$ mice using the students T test, n=4 for ADA$^+$ mice, n=8 for ADA$^{-/-}$ mice, n=not detected.
Figure 4B:
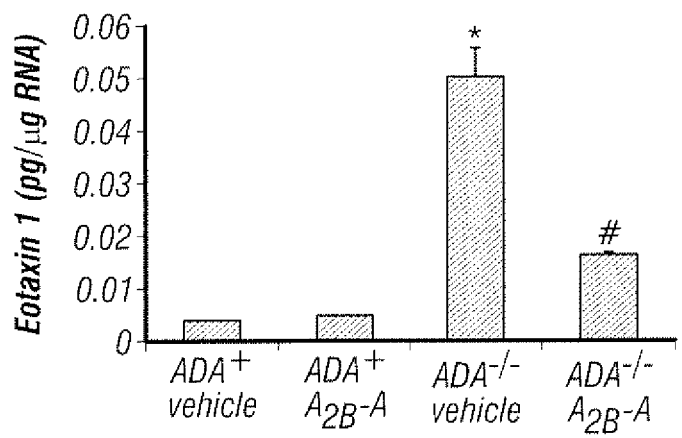
Figure 4C:
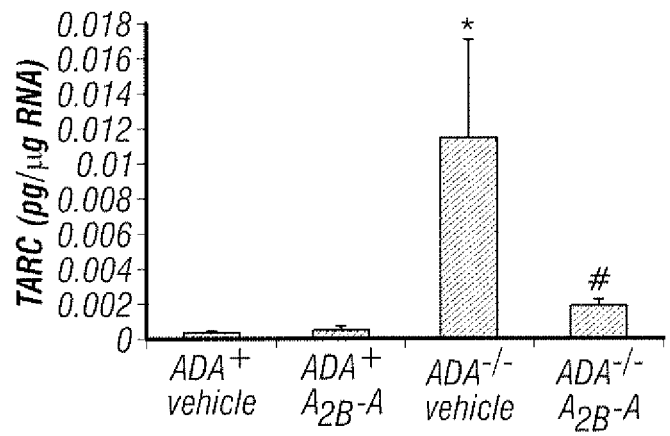

The ability of adenosine $A_{2B}$ antagonist treatment to dampen the degree of pulmonary inflammation in $ADA^{-/-}$ mice prompted the examination of the levels of key cytokines and chemokines. Whole lung RNA extracts from $ADA^+$ and $ADA^{-/-}$ mice treated with vehicle or an $A_{2B}$ adenosine receptor antagonist were analyzed. IL-5, IL-4, TNFα, RANTES and various monocyte chemoatraetant proteins (MCPs) were found to be elevated in the lungs of $ADA^{-/-}$ mice treated with vehicle; however their levels did not change with $A_{2B}$ adenosine receptor antagonist treatment. In contrast, IL-6, Eotaxin I and TARC were elevated in vehicle treated $ADA^{-/-}$ mice and their levels were significantly lower in $ADA^{-/-}$ mice treated with the $A_{2B}$ adenosine receptor antagonist. As shown in FIG. 4, these findings demonstrate that $A_{2B}AR$ antagonism in $ADA^{-/-}$ mice is able to prevent the expression of certain but not all pro-inflammatory cytokines and chemokines.

The Effect on Myofibroblast Accumulation

Figure 5A:
FIG. 5 shows the results of α-smooth muscle actin immunostaining. Lung sections were stained with antiserum against α-smooth muscle actin to visualize myofibroblast (brown). (A) Lung from an ADA$^+$ vehicle treated mouse. (B) Lung from an ADA$^{-/-}$ vehicle treated mouse. (C) Lung from an ADA$^{-/-}$ adenosine $A_{2B}$ receptor antagonist treated mouse. Sections are representative of 6 different mice from each treatment. Scale bar=100 µm.
Figure 5B:
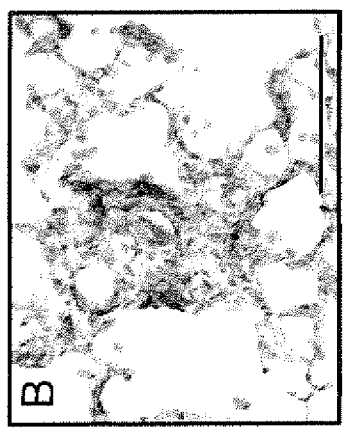
Figure 5C:
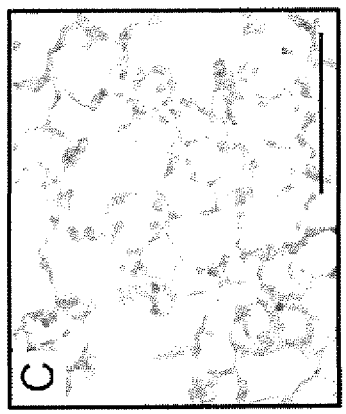

Previous studies have demonstrated that $ADA^{-/-}$ mice develop pulmonary fibrosis in conjunction with adenosine elevations. To determine the effect of an adenosine $A_{2B}$ receptor antagonist treatment on pulmonary fibrosis in $ADA^{-/-}$ mice the status of pulmonary myofibroblasts were examined by staining for α-smooth muscle actin (α-sma) (FIG. 5). No α-sma positive cells were seen in the distal airways of $ADA^+$ vehicle treated mice (FIG. 5A), whereas α-sma staining was prominent in the distal airways of vehicle treated $ADA^{-/-}$ mice (FIG. 5B). Few to no α-sma positive cells were seen in the distal airways of $ADA^{-/-}$ mice treated with an adenosine $A_{2B}$ receptor antagonist (FIG. 5C), suggesting $A_{2B}AR$ antagonism can prevent the accumulation of myofibroblasts in the lung of $ADA^{-/-}$ mice.

Effects on Collagen Deposition

Figure 6A:
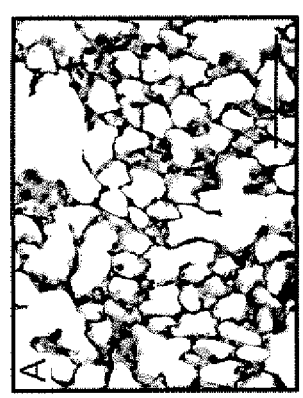
FIG. 6 depicts collagen deposition in the lungs of adenosine $A_{2B}$ receptor antagonist-treated ADA−/− mice as described in Example 21. Lung sections were stained with Masson's Trichrome to visualize collagen deposition (blue). (A) Lung from an ADA$^+$ vehicle treated mouse. (B) Lung from an ADA$^+$ adenosine $A_{2B}$ receptor antagonist treated mouse. (C) Lung from an ADA$^{-/-}$ vehicle treated mouse. (D) Lung from an ADA$^{-/-}$ adenosine $A_{2B}$ receptor antagonist treated mouse. Sections are representative of 6 different mice from each treatment. Scale bar=100 µm. (E) α-1 procollagen transcript levels are presented as mean pg transcripts/µg RNA±SEM. *, significant at p<0.05 compared to ADA$^+$ animals using the students T test; #, significant at p<0.05 compared to vehicle-treated ADA$^{-/-}$ mice using the students T test, n=4 for ADA$^+$ mice, n=8 for ADA$^{-/-}$ mice. (F) Soluble collagen protein levels presented as mean µg collagen per ml BAL fluid±SEM. *, significant at p<0.05 compared to ADA$^+$ animals using the students T test; #, significant at p<0.05 compared to vehicle-treated ADA$^{-/-}$ mice using the students T test, n=4 for ADA$^+$ mice, n=8 for ADA$^{-/-}$ mice.
Figure 6B:
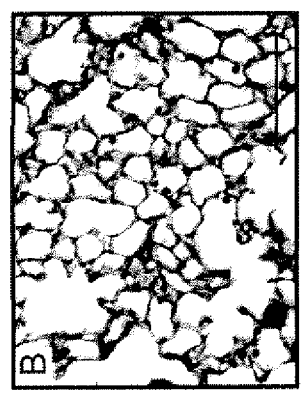
Figure 6C:
Figure 6D:
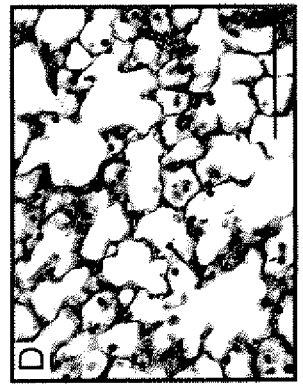
Figure 6E:
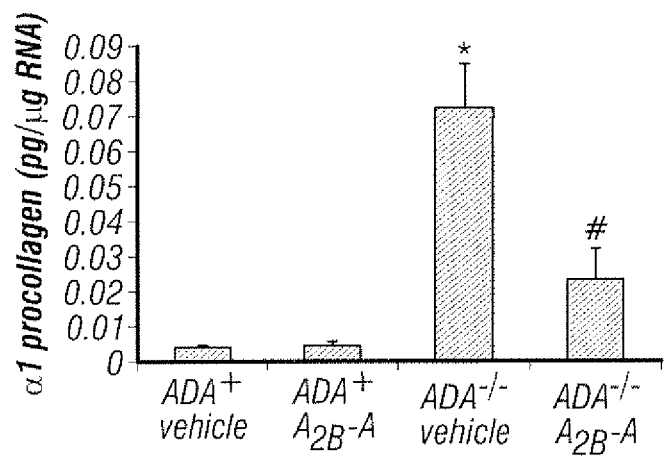
Figure 6F:
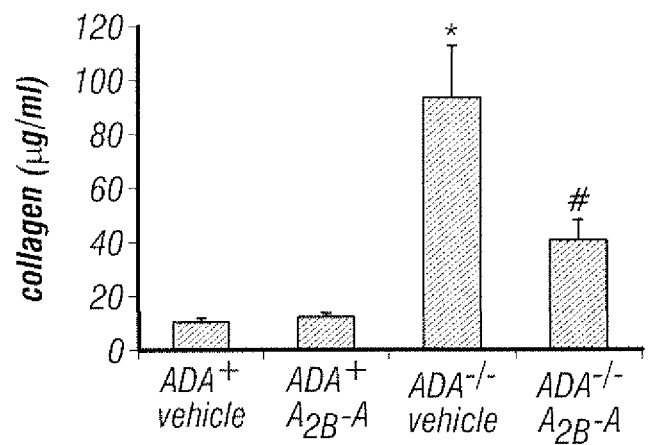

Previous work in the ADA-/- model has demonstrated that ADA-/- mice develop severe pulmonary fibrosis in conjunction with adenosine elevations. To determine the effect of $A_{2B}$ adenosine receptor antagonist treatment on fibrosis in ADA-/- mice we examined the degree of collagen deposition using Mason's trichrome staining (FIG. 6). Examination of collagen deposition revealed that there was little to no collagen deposition in the lungs of $ADA^+$ vehicle or adenosine $A_{2B}$ receptor antagonist treated mice (FIG. 6A and B), whereas distal airway collagen deposition was prominent in vehicle treated $ADA^{-/-}$ mice (FIG. 6C). Treatment of $ADA^{-/-}$ mice with the adenosine $A_{2B}$ receptor antagonist 3-ethyl-1-propyl-8-{1-[(3-trifluoromethylphenyl)methyl]pyrazol -4-yl{-1,3,7-trihydropurine-2,6-dione resulted in a reduction in collagen deposition in the airways (FIG. 6D). Collagen production was measured by quantifying whole lung α1-procollagen transcript levels (FIG. 6E) and collagen protein levels in BAL fluid (FIG. 6F). Significant increases in collagen production were seen in the lungs of $ADA^{-/-}$ mice treated with vehicle, and these increases were largely prevented by CVT-6883 treatment. These findings demonstrate that adenosine $A_{2B}$ receptor antagonists can prevent the development of fibrosis in $ADA^{-/-}$ mice and implicate $A_{2B}AR$ signaling in the regulation of pulmonary fibrosis.

Reduction in Profibrotic Mediators

Figure 7A:
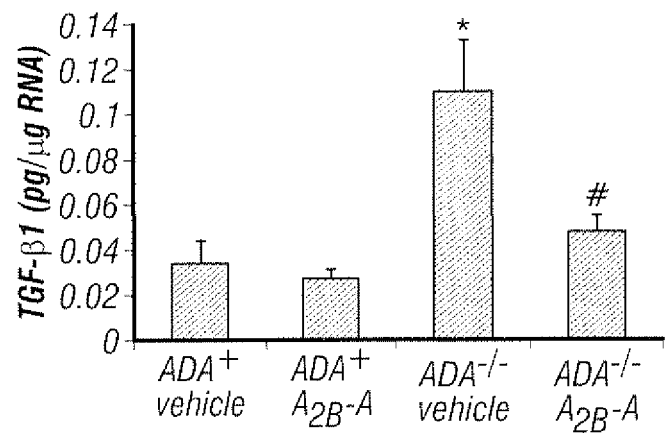
FIG. 7 shows the expression of fibrosis associated genes. RNA was extracted from whole lungs for analysis using quantitative RT-PCR for various fibrosis associated transcripts. Results demonstrate that lungs from an adenosine $A_{2B}$ receptor antagonist treated ADA$^{-/-}$ mice exhibit lower levels of transcripts for TGF-β1 (A), osteopontin (OPN) (B), and plasminogen activator inhibitor-1 (Pai-1) (C), as compared to that seen in the lungs of vehicle treated ADA$^{-/-}$ mice. *, significant at p<0.05 compared to ADA$^+$ mice using the students T test, #, significant at p<0.05 compared to vehicle-treated ADA$^{-/-}$ mice using the students T test, n=4 for ADA+ mice, n=8 for ADA mice.
Figure 7B:
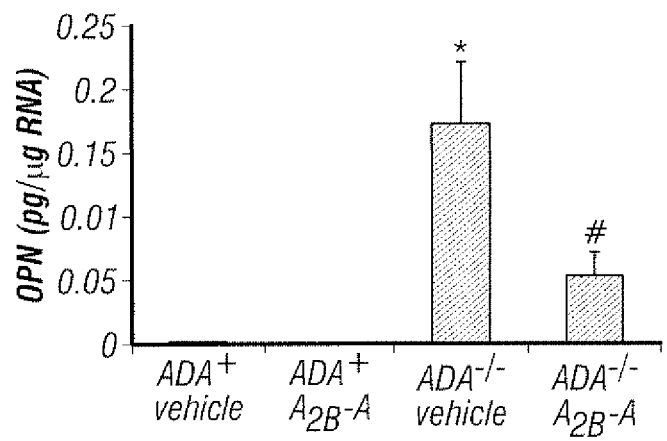
Figure 7C:
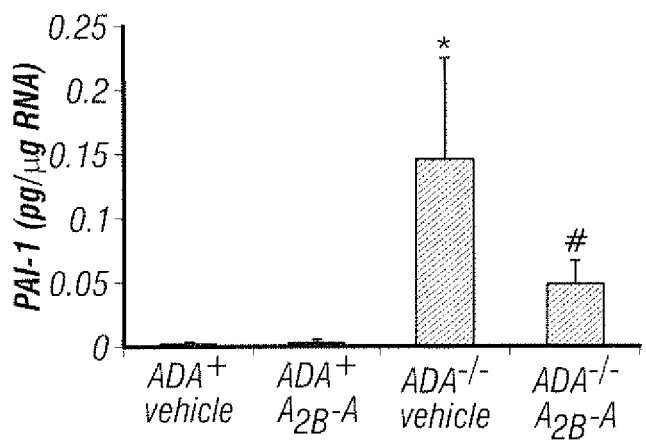

TGF-β1, osteopontin (OPN) and plasminogen activator inhibitor-1 (PAI-1) are pro-fibrotic mediators that have been shown to be elevated in the lungs of $ADA^{-/-}$ mice (Chunn et al (2005) *J Immunol* 175:1937-1946). The levels of these fibrotic regulators were elevated in the lungs of $ADA^{-/-}$ mice treated with vehicle, while adenosine $A_{2B}$ receptor antagonist treatment decreased expression of these molecules (FIG. 7). These findings suggest that $A_{2B}AR$ antagonism can prevent the expression of key regulators of fibrosis in the lungs of $ADA^{-/-}$ mice.

Normalization of Protease/Anti-Protease Levels

Figure 8A:
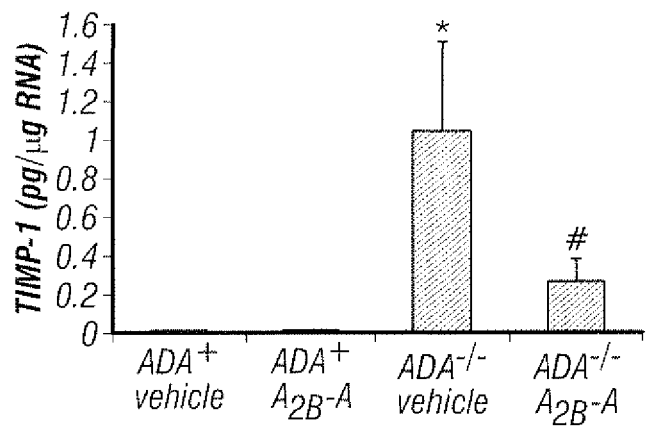
FIG. 8 shows the elevation of genes associated with alveolar airway destruction. Transcript levels of TIMP-1, MMP-9, and MMP-12 were measured in whole lung RNA extracts using quantitative RT-PCR. (A) TIMP-1. (B) MMP-9. (C) MMP-12. Data are presented as mean pg of transcripts/µg RNA±SEM. *, significant at p<0.05 compared to ADA$^+$ mice using the students T test, #, significant at p<0.05 compared to vehicle-treated ADA$^{-/-}$ mice using the students T test. n=4 for ADA$^+$ mice, n=8 for ADA$^{-/-}$ mice.
Figure 8B:
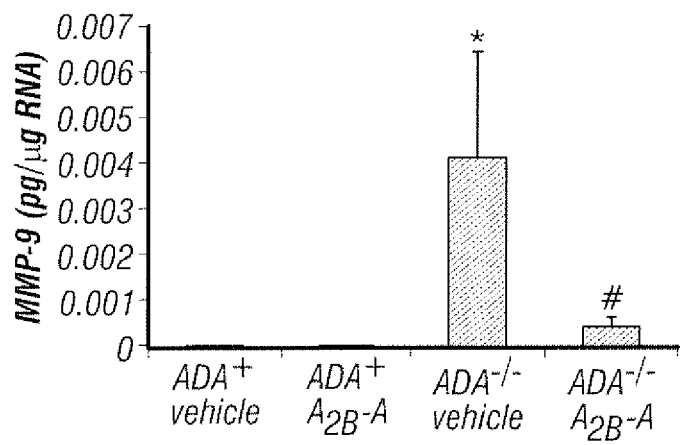
Figure 8C:
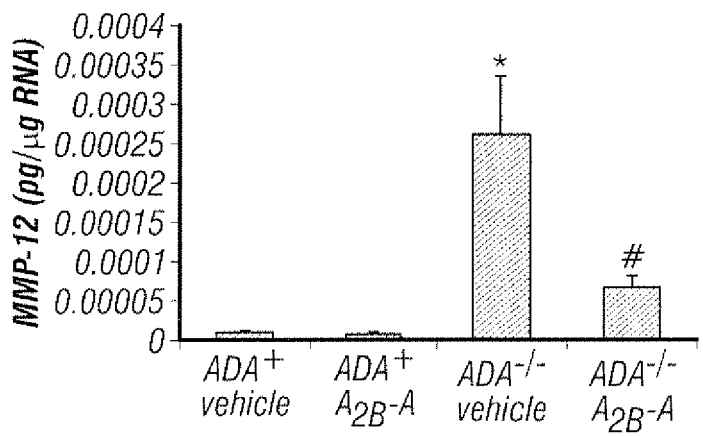

Increased levels of metalloproteinases (MMPs) and inhibitors of proteases are features of distal airway enlargement in many models including $ADA^{-/-}$ mice (Sun et al. (2005) *J Clin Invest* 115:35-43, Hautamaki et al. (1997) *Science* 277:2002-2004, Lanone et al. (2002) *J Clin Invest* 110:463-474). Examination of anti-proteases and proteases in the lungs of $ADA^{-/-}$ mice treated with vehicle demonstrated an increase in the expression of TIMP-1, MMP-9 and MMP-12 (FIG. 8). Treatment of $ADA^{-/-}$ mice with an adenosine $A_{2B}$ receptor antagonist led to diminished expression of all three of these regulators of alveolar integrity, suggesting that $A_{2B}AR$ signaling is involved in regulating adenosine-induced protease and anti-protease expression in the lungs of $ADA^{-/-}$ mice.

Effects on Alveolar Destruction

Figure 9A:
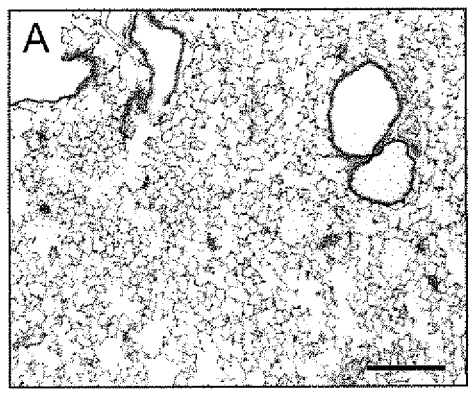
FIG. 9 presents alveolar destruction in ADA−/− mice treated with an adenosine $A_{2B}$ receptor antagonist as described in Example 21. Lungs were collected and processed for histological analysis using H&E staining. (A) Lung from ADA+ vehicle treated mouse, (B) Lung from ADA−/− vehicle treated mouse, and (C) Lung from ADA−/− mouse treated with an adenosine $A_{2B}$ receptor antagonist. Photographs were all taken at the same magnification (10×) and represent findings from 6 different animals for each treatment group. (D) Alveolar airway sizes were calculated using ImagePro and data is presented as mean cord length±SEM, n=6. In (F), * denotes that the results are significantly different form ADA+ mice and ** denotes that results are significantly different from ADA−/− vehicle treated mice.
Figure 9B:
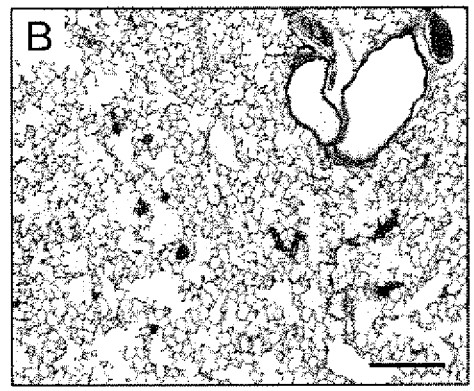
Figure 9C:
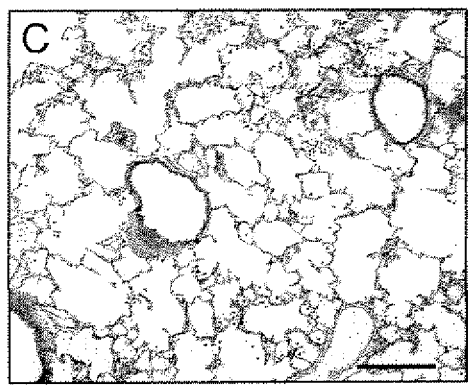
Figure 9D:
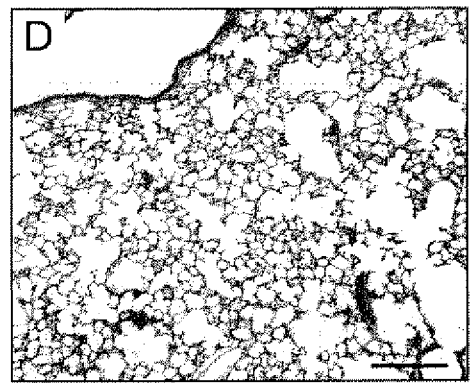
Figure 9E:
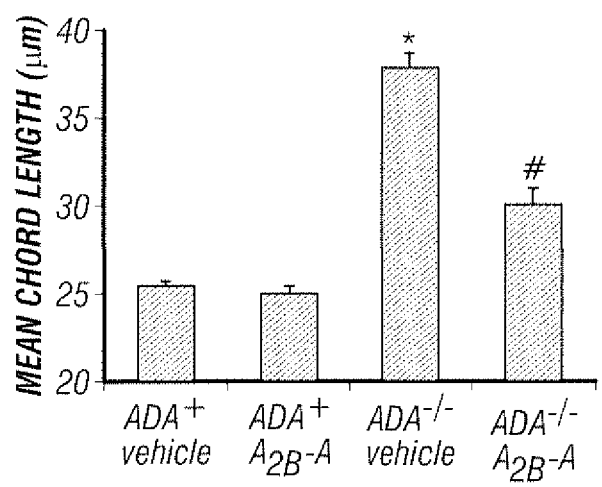

ADA-/- mice develop features of distal airway enlargement characteristic of emphysema that are mediated by elevations in lung adenosine levels. To examine the effect of 3-ethyl-1-propyl-8-(1-{[3-(trifluoromethyl)phenyl]methyl} (4-hydropyrazol-4-yl))-1,3,7-trihydropurine-2,6-dione on the distal airway enlargement seen in ADA-/- mice, alveolar destruction was assessed histologically and by determining mean cord length size of the distal airways (FIG. 9). The airways of ADA+ animals were well ordered and small when viewed histologically (FIG. 9A). ADA-/- airways were enlarged (FIG. 9B) and treatment of ADA-/- mice with 3-ethyl-1-propyl-8-(1-{[3-(trifluoromethyl)phenyl]methyl} (4-hydropyrazol-4-yl))-1,3,7-trihydropurine-2,6-dione prevented this enlargement (FIG. 9C). Quantification of distal airway size agreed with the histological observations (FIG. 9D). These data demonstrate that treatment of ADA-/- mice with 3-ethyl-1-propyl-8-(1-{[3-(trifluoromethyl)phenyl]methyl}(4-hydropyrazol-4-yl))-1,3,7-trihydropurine-2,6-dione can prevent the alveolar airway destruction seen in ADA-/- mice

We claim:

1. A method for the treatment of chronic obstructive pulmonary disease (COPD), said method comprising administering to a mammal in need thereof a pharmaceutical composition comprising a therapeutically effective amount of 3-ethyl-1-propyl-8- {1- [(3-trifluoromethylphenyl)methyl] pyrazol-4-yl}-1,3,7-trihydropurine-2,6-dione, having the chemical structure

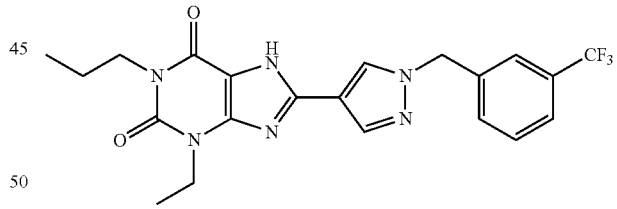

wherein an $A_3$ adenosine receptor antagonist is not administered to said mammal.

2. The method of claim 1, wherein the administration is oral.

3. The method of claim 1, wherein the administration is intravenous.

4. The method of claim 1, wherein the administration is intramuscular.

5. The method of claim 1, wherein the administration is intraperitoneal.

6. The method of claim 1, wherein the administration is by inhalation.

* * * * *